(12) United States Patent
Wong et al.

(10) Patent No.: US 7,989,593 B1
(45) Date of Patent: *Aug. 2, 2011

(54) METHOD FOR THE PREPARATION OF A HIGH-TEMPERATURE STABLE OXYGEN-CARRIER-CONTAINING PHARMACEUTICAL COMPOSITION AND THE USE THEREOF

(76) Inventors: Bing Lou Wong, Irvine, CA (US); Sui Yi Kwok, Hong Kong (HK)

( * ) Notice: Subject to any disclaimer, the term of this patent is extended or adjusted under 35 U.S.C. 154(b) by 0 days.
This patent is subject to a terminal disclaimer.

(21) Appl. No.: 13/083,639

(22) Filed: Apr. 11, 2011

Related U.S. Application Data

(63) Continuation-in-part of application No. 13/013,847, filed on Jan. 26, 2011.

(60) Provisional application No. 61/348,764, filed on May 27, 2010.

(51) Int. Cl.
C07K 14/00 (2006.01)
C07K 14/805 (2006.01)
A61K 49/14 (2006.01)

(52) U.S. Cl. ....... 530/385; 514/1.1; 514/13.4; 514/13.5; 514/15.1

(58) Field of Classification Search ................. None
See application file for complete search history.

(56) References Cited

U.S. PATENT DOCUMENTS

| | | |
|---|---|---|
| 4,529,719 A | 7/1985 | Tye |
| 4,543,209 A | 9/1985 | Tayot et al. |
| 4,598,064 A | 7/1986 | Walder |
| 4,600,531 A | 7/1986 | Walder |
| 4,831,012 A | 5/1989 | Estep |
| 4,987,048 A | 1/1991 | Shinozaki et al. |
| 5,084,558 A | 1/1992 | Rausch et al. |
| 5,189,146 A | 2/1993 | Hsia |
| RE034,271 E | 6/1993 | Walder |
| 5,250,665 A | 10/1993 | Kluger et al. |
| 5,296,465 A | 3/1994 | Rausch et al. |
| 5,344,393 A | 9/1994 | Roth et al. |
| 5,439,882 A | 8/1995 | Feola et al. |
| 5,451,205 A | 9/1995 | Roth et al. |
| 5,591,710 A | 1/1997 | Hsia |
| 5,618,919 A | 4/1997 | Rausch et al. |
| 5,631,219 A | 5/1997 | Rosenthal et al. |
| 5,691,453 A | 11/1997 | Wertz et al. |
| 5,725,839 A | 3/1998 | Hsia |
| 5,741,893 A | 4/1998 | Hsia |
| 5,753,616 A | 5/1998 | Rausch et al. |
| 5,767,089 A | 6/1998 | Hsia |
| 5,789,376 A | 8/1998 | Hsia |
| 5,804,561 A | 9/1998 | Hsia |
| 5,807,831 A | 9/1998 | Hsia |
| 5,811,005 A | 9/1998 | Hsia |
| 5,814,601 A | 9/1998 | Winslow et al. |
| 5,817,528 A | 10/1998 | Bohm et al. |
| 5,817,632 A | 10/1998 | Hsia |
| 5,824,781 A | 10/1998 | Hsia |
| 5,840,701 A | 11/1998 | Hsia |
| 5,840,851 A | 11/1998 | Plomer et al. |
| 5,865,784 A | 2/1999 | Faithfull et al. |
| 5,895,810 A | 4/1999 | Light et al. |
| 5,905,141 A | 5/1999 | Rausch et al. |
| 5,955,581 A | 9/1999 | Rausch et al. |
| 6,007,774 A | 12/1999 | Faithfull et al. |
| 6,054,427 A | 4/2000 | Winslow |
| 6,127,043 A | 10/2000 | Lange |
| 6,160,098 A | 12/2000 | Kerwin |
| 6,242,417 B1 | 6/2001 | Gerber et al. |
| 6,270,952 B1 | 8/2001 | Cook et al. |
| 6,288,027 B1 | 9/2001 | Gawryl et al. |
| 6,323,175 B1 | 11/2001 | Hsia |
| 6,399,357 B1 | 6/2002 | Winge |
| 6,432,918 B1 | 8/2002 | Winslow |
| 6,486,306 B1 | 11/2002 | Winge |
| 6,506,725 B1 | 1/2003 | Rausch et al. |
| RE038,081 E | 4/2003 | Faithfull et al. |
| 6,566,504 B2 | 5/2003 | Bhattacharya et al. |
| 6,599,878 B2 | 7/2003 | Rooney |
| 6,610,832 B1 | 8/2003 | Gawryl et al. |
| 6,709,810 B2 | 3/2004 | Cook et al. |
| 6,740,139 B2 | 5/2004 | Russell et al. |
| 6,747,132 B2 | 6/2004 | Privalle et al. |
| 6,844,317 B2 | 1/2005 | Winslow et al. |
| 6,894,150 B1 | 5/2005 | Tye |

(Continued)

OTHER PUBLICATIONS

Malavalli, J. of Protein Chemistry, vol. 19, No. 4, 2000, pp. 255-267.
Hu, Biochem. J. vol. 402, 2007, pp. 143-151.
Jones, J. of Biological Chemistry, vol. 271, No. 2, 1996, pp. 675-680.
Chatterjee, J. of Biological Chemistry, vol. 261, No. 21, 1986, pp. 9929-9937.
Ji, Proteins: Structure, Function, and Genetics, vol. 30, 1998, pp. 309-320.
Kavanaugh, Biochemistry, vol. 27, 1988, pp. 1804-1808.
Kwansa, Proteins: Structure, Function, and Genetics, vol. 39, 2000, pp. 166-169.
Manning, Proc. Nat'l. Acad. Sci. USA, vol. 88, 1991, pp. 3329-3333.
Snyder, Proc. Nat'l. Acad. Sci, USA, vol. 84, 1987, pp. 7280-7284.
Napolitano LM., "Hemoglobin-based oxygen carriers: first, second or third generation? Human or bovine? Where are we now?", Crit Care Clin. 25, 279-301 (2009).
Jiin-Yu Chen et al., "A review of blood substitutes: examining the history, clinical trial results, and ethics of hemoglobin-based oxygen carriers", Clinics 64(8), 803-813 (2009).

(Continued)

Primary Examiner — Anand Desai
(74) Attorney, Agent, or Firm — Ella Cheong, Hong Kong, Ltd.; Margaret Burke; Sam Yip

(57) ABSTRACT

A high temperature-stable and highly purified cross-linked (optionally ≧70% β-β linked) tetrameric hemoglobin with high efficiency of oxygen delivery suitable for use in mammals without causing renal injury and vasoconstriction is provided. The dimeric form of hemoglobin is degenerated and purification processes are performed on red blood cells from whole blood. Controlled hypotonic lysis in an instant cytolysis apparatus prevents lysis of white blood cells. Nucleic acids from white blood cells and phospholipids impurities are not detected. Blocking of reactive sulfhydryl groups by a sulfhydryl reagent is performed in an oxygenated environment. Flowthrough column chromatography removes different plasma protein impurities. N-acetyl cysteine is added to the cross-linked tetrameric hemoglobin to maintain a low level of met-hemoglobin. The stabilized hemoglobin is preserved in an infusion bag with aluminum overwrap to prevent formation of inactive met-hemoglobin from oxygen intrusion. The product finds use in tissue oxygenation and cancer treatment.

13 Claims, 18 Drawing Sheets

U.S. PATENT DOCUMENTS

| | | | |
|---|---|---|---|
| 7,038,016 | B2 | 5/2006 | Talarico et al. |
| 7,101,846 | B2 | 9/2006 | Winslow |
| 7,293,985 | B2 | 11/2007 | Cook et al. |
| 7,411,044 | B2 | 8/2008 | Avella et al. |
| 7,435,795 | B2 | 10/2008 | McGinnis et al. |
| 7,494,974 | B2 | 2/2009 | Tye |
| 7,501,499 | B2 | 3/2009 | Acharya et al. |
| 7,504,377 | B2 | 3/2009 | Tye |
| 7,553,613 | B2 | 6/2009 | Gawryl et al. |
| 7,625,862 | B2 | 12/2009 | Winslow et al. |
| 7,655,392 | B2 | 2/2010 | Stassinopoulos |
| 7,759,306 | B2 | 7/2010 | Simoni et al. |
| 7,795,401 | B2 | 9/2010 | Huang et al. |
| 7,932,356 | B1 | 4/2011 | Wong et al. |
| 2007/0142626 | A1 | 6/2007 | Kluger et al. |

OTHER PUBLICATIONS

Lamy ML et al., "Randomized Trial of Diaspirin Cross-linked Hemoglobin Solution as an Alternative to Blood Transfusion after Cardiac Surgery", Anesthesiology 92(3), 646-656 (2000).

Lois R. Manning et al., "Subunit dissociations in natural and recombinant hemoglobins", Protein Science 5(4), 775-781 (1996).

Ronald Kluger et al., "Protein-protein coupling and its application to functional red cell substitutes", Chem Commun (Camb). 46(8), 1194-1202 (2010).

Ronald Kluger, "Red cell substitutes from hemoglobin—do we start all over again?", Current Opinion in Chemical Biology 14(4), 538-543 (2010).

Kenji Sampel et al., "Role of nitric oxide scavenging in vascular response to cell-free hemoglobin transfusion", Am J Physiol Heart Circ Physiol 289(3), H1191-H1201 (2005).

Tao Hu et al., "Preparation and characterization of dimeric bovine hemoglobin tetramers", Journal of Protein Chemistry 22(5), 411-416(2003).

Tao Hu et al., "PEGylation of Val-1(alpha) destabilizes the tetrameric structure of hemoglobin", Biochemistry 48(3), 608-616 (2009).

Kim D Vandegriff et al., "Hemospan: design principles for a new class of oxygen therapeutic", Artificial organs 33(2), 133-138 (2009).

Thoralf Kerner et al., "DCL-Hb for trauma patients with severe hemorrhagic shock: the European "On-Scene" multicenter study", Intensive Care Medicine 29(3), 378-385 (2003).

Chad R, Haney et al., "Purification and chemical modifications of hemoglobin in developing hemoglobin based oxygen carriers", Advanced Drug Delivery Reviews 40(3), 153-169 (2000).

Donat R. Spahn et al., "Artificial O2 carriers : Status in 2005", Current pharmaceutical design 11(31), 4099-4114 (2005).

Andre F. Palmer et al., "Tangential flow filtration of hemoglobin", Biotechnol Prog. 25(1), 189-199 (2009).

David C. Irwin et al., "Polymerized bovine hemoglobin decreases oxygen delivery during normoxia and acute hypoxia in the rat", Am J Physiol Heart Circ Physiol 295(3), H1090-H1099 (2008).

Guoyong Sun et al, "Preparation of Ultrapure Bovine and Human Hemoglobin by Anion Exchange Chromatography", J Chromatogr B Analyt Technol Biomed Life Sci. 867(1), 1-7 (2008).

Ylping Jia et al., "Effects of cross-linking and zero-link polymerization on oxygen transport and redox chemistry of bovine hemoglobin", Biochimica et Biophysica Acta 1794(8), 1234-1242 (2009).

Cai Jin et al., "Chemically Modified Porcine Hemoglobins and Their Biological Properties", Protein and Peptide Letters, vol. 11, No. 4, 353-360 (2004).

Alpha hemoglobin chain

```
B  -VLSAADKGNVKAAWGKVGGHAAEYGAEALERMFLSFPTTKTYFPHFDLSHGSAQVKGHGAKVAAALTKAVEHLDDLPGA  79
H  MVLSPADKTNVKAAWGKVGAHAGEYGAEALERMFLSFPTTKTYFPHFDLSHGSAQVKGHGKKVADALTNAVAHVDDMPNA  80
C  -VLSPADKTNIKSTWDKIGGHAGDYGGEALDRTFQSFPTTKTYFPHFDLSPGSAQVKAHGKKVADALTTAVAHLDDLPGA  79
P  -VLSAADKADVKAAYGKVGAHAGEAGAEALERMFLGFTTTKTYFPHFDLSHGSDEVKAHGEKVADALTKAVGHLDDMPGA  79
E  MVLSAADKTNVKAAWSKVGGHAGEFGAEALERMFLGFPTTKTYFPHFDLSHGSAQVKAHGKKVGDALTLAVGHLDDLPGA  80

B  LSELSDLHAHKLRVDPVNFKLLSHSLLVTLASHLPSDFTPAVHASLDKFLANVSTVLTSKYR  141
H  LSALSDLHAHKLRVDPVNFKLLSHCLLVTLAAHLPAEFTPAVHASLDKFLASVSTVLTSKYR  142
C  LSALSDLHAYKLRVDPVNFKLLSHCLLVTLACHHPTEFTPAVHASLDKFFAAVSTVLTSKYR  141
P  LSALSDLHAHKLRVDPVDFKLLSHCLLSTLAVHLPDDFTPAVHADLDKFLADVSTVLDSKYR  141
E  LSNLSDLHAHKLRVDPVNFKLLSHCLLSTLAVHLPNDFTPAVHASLDKFLSSVSTVLTSKYR  142
```

Beta hemoglobin chain

```
B  M--LTAEEKAAVTAFWGKVKVDEVGGEALGRLLVVYPWTQRFFESFGDLSTADAVMNNPKVKAHGKKVLDSFSNGMKHLD  78
H  MVHLTPEEKSAVTALWGKVNVDEVGGEALGRLLVVYPWTQRFFESFGDLSTPDAVMGNPKVKAHGKKVLGAFSDGLAHLD  80
P  MVHLSAEEKEAVLGLWGKVNVDEVGGEALGRLLVVYPWTQRFFESFGDLSNADAVMGNPKVKAHGKKVLQSFSDGLKHLD  80
E  MVQLSGEEKAAVLALWDKVNEEEVGGEALGRLLVVYPWTQRFFDSFGDLSNPGAVMGNPKVKAHGKKVLHSFGEGVHHLD  80

B  DLKGTFAALSELHCDKLHVDPENFKLLGNVLVVVLARNFGKEFTPVLQADFQKVVAGVANALAHRYH  145
H  NLKGTFATLSELHCDKLHVDPENFRLLGNVLVCVLAHHFGKEFTPPVQAAYQKVVAGVANALAHKYH  147
P  NLKGTFAKLSELHCDQLHVDPENFRLLGNVIVVVLARRLGHDFNPNVQAAFQKVVAGVANALAHKYH  147
E  NLKGTFAALSELHCDKLHVDPENFRLLGNVLVVVLARHFGKDFTPELQASYQKVVAGVANALAHKYH  147
```

FIG. 1

METHOD FOR THE PREPARATION OF A HIGH-TEMPERATURE STABLE OXYGEN-CARRIER-CONTAINING PHARMACEUTICAL COMPOSITION AND THE USE THEREOF

CROSS-REFERENCE TO RELATED APPLICATION

This application claims priority of U.S. provisional patent application No. 61/348,764 filed on May 27, 2010 and U.S. patent application Ser. No. 13/013,847 filed on 26 Jan., 2011, the disclosures of which are incorporated by reference.

TECHNICAL FIELD

The present invention relates to a method for the preparation of a high-temperature stable oxygen-carrier-containing pharmaceutical composition and the composition made by the process. The present invention also relates to the use of the high-temperature stable oxygen carrier-containing pharmaceutical composition for cancer treatment, oxygen-deprivation disorder and organ preservation for humans and other animals.

BACKGROUND OF INVENTION

Hemoglobin plays an important role in most vertebrates for gaseous exchange between the vascular system and tissue. It is responsible for carrying oxygen from the respiratory system to the body cells via blood circulation and also carrying the metabolic waste product carbon dioxide away from body cells to the respiratory system, where the carbon dioxide is exhaled. Since hemoglobin has this oxygen transport feature, it can be used as a potent oxygen supplier if it can be stabilized ex vivo and used in vivo.

Naturally-occurring hemoglobin is a tetramer which is generally stable when present within red blood cells. However, when naturally-occurring hemoglobin is removed from red blood cells, it becomes unstable in plasma and splits into two $\alpha$-$\beta$ dimers. Each of these dimers is approximately 32 kDa in molecular weight. These dimers may cause substantial renal injury when filtered through the kidneys and excreted. The breakdown of the tetramer linkage also negatively impacts the sustainability of the functional hemoglobin in circulation.

In order to prevent breakdown of the tetramer, recent developments in hemoglobin processing have incorporated various cross-linking techniques to create intramolecular bonds within the tetramer as well as intermolecular bonds between the tetramers to form polymeric hemoglobin. The prior art teaches that polymeric hemoglobin is the preferred form in order to increase circulatory half-life of the hemoglobin. However, as determined by the present inventors, polymeric hemoglobin more readily converts to met-hemoglobin in blood circulation. Met-hemoglobin cannot bind oxygen and therefore cannot oxygenate tissue. Therefore, the cross-linking taught by the prior art that causes the formation of polymeric hemoglobin is a problem. There is a need in the art for a technique that permits intramolecular crosslinking to create stable tetramers without the simultaneous formation of polymeric hemoglobin.

Further problems with the prior art attempts to stabilize hemoglobin include production of tetrameric hemoglobin that includes an unacceptably high percentage of dimer units; the presence of dimers makes the hemoglobin composition unsatisfactory for administration to mammals. The dimeric form of the hemoglobin can cause severe renal injury in a mammalian body; this renal injury can be severe enough to cause death. Therefore, there is a need in the art to create stable tetrameric hemoglobin with low unwanted dimeric form in the final product.

Further problems with prior art attempts to create stable hemoglobin include the presence of protein impurities such as immunoglobin G that can cause allergic effects in mammals. Therefore, there is a need in the art for a process which can produce stable tetrameric hemoglobin without protein impurities.

Other problems with prior art hemoglobin preparations include vasoconstriction following transfusion in mammals. It has been indicated that this vasoconstriction is due to endothelium-derived relaxing factor binding to reactive sulfhydryl groups of a hemoglobin molecule. Thus, there is a need in the art to create a stabilized tetrameric hemoglobin that does not cause vasoconstriction following transfusion.

In addition to the above problems, there is a need in the art for a stabilized tetrameric hemoglobin that is phospholipid free and capable of production on an industrial scale.

SUMMARY OF INVENTION

The present invention provides a method for producing high-temperature stable, purified, cross-linked tetrameric hemoglobin suitable for use in mammals without causing severe renal injury, vascular detrimental effects, or other severe adverse effects (including death). The invention also includes the high-temperature stable, purified, cross-linked tetrameric hemoglobin and the use of the hemoglobin for oxygenation of in vivo and ex vivo tissue.

The method includes a starting material of mammalian whole blood including at least red blood cells and plasma. Red blood cells are separated from the plasma in the mammalian whole blood followed by filtering to obtain a filtered red blood cell fraction. The filtered red blood cell fraction is washed to remove plasma protein impurities. The washed red blood cells are disrupted by a controlled hypotonic lysis for a time sufficient to lyse red blood cells without lysing white blood cells in an instant cytolysis apparatus at a flow rate of at 50-1000 liter/hr. Filtration is performed to remove at least a portion of the waste retentate from the lysate. A first hemoglobin solution is extracted from the lysate.

A first ultrafiltration process is performed using an ultrafiltration filter configured to remove impurities having a higher molecular weight than tetrameric hemoglobin and to further remove any viruses and residual waste retentate from the first hemoglobin solution to obtain a second hemoglobin solution. Flowthrough column chromatography is performed on the second hemoglobin solution to remove protein impurities, dimeric hemoglobin and phospholipids to form a phospholipid-free and low dimer hemoglobin solution. A second ultrafiltration process is performed on the phospholipid-free and low dimer hemoglobin solution using a filter configured to remove impurities resulting in a concentrated purified phospholipid-free and low dimer hemoglobin solution.

Sulfhydryl groups of hemoglobin molecules are blocked in the concentrated, purified phospholipid-free and low dimer hemoglobin solution by a sulfhydryl reagent in a fully oxygenated environment. The resultant hemoglobin molecules each have at least one cysteine moiety including a thiol-protecting group such that the hemoglobin molecules are incapable of binding endothelium-derived relaxing factor at the cysteine site.

At least the α-α and/or β-β subunits of the thiol-protected hemoglobin are cross-linked by bis-3,5-dibromosalicy fumarate to form high-temperature stable cross-linked tetrameric hemoglobin without the formation of polymeric hemoglobin such that the molecular weight of the resultant cross-linked tetrameric hemoglobin is 60-70 kDa. A suitable physiological buffer is exchanged for the cross-linked tetrameric hemoglobin. Any residual non-cross-linked tetrameric hemoglobin and any residual chemicals are removed by using tangential-flow ultrafiltration. N-acetyl cysteine is added at a concentration of 0.2-0.4% to the cross-linked tetrameric hemoglobin to maintain a level of met-hemoglobin below 5%. The phospholipid-free, low dimer, thiol-protected high-temperature stable cross-linked tetrameric hemoglobin is then added to a pharmaceutically acceptable carrier; the pharmaceutically acceptable carrier can be a physiological buffer or water.

Following this procedure, the resultant hemoglobin is optionally packaged in air-tight polyethylene, ethylene-vinyl-acetate, ethylene-vinyl alcohol (PE, EVA, EVOH) infusion packages. The packaging prevents oxygen contamination which results in the formation of inactive met-hemoglobin.

The high-temperature stable cross-linked hemoglobin produced by the above method is used for the treatment of various cancers such as leukemia, colorectal cancer, lung cancer, breast cancer, nasopharyngeal cancer and esophageal cancer. The mechanism for destroying cancer cells is to improve oxygenation in tumor cells, thereby enhancing the sensitivity towards radiation and chemotherapeutic agents. The high-temperature stable cross-linked tetrameric hemoglobin is also used for preservation of organ tissue during transplant or for preservation of the heart in situations where there is a lack of oxygen supply in vivo, such as in an oxygen-deprived heart.

BRIEF DESCRIPTION OF THE DRAWINGS

FIG. 1 shows the amino acid sequences alignment of bovine, human, canine, porcine and equine hemoglobin, respectively labeled B, H, C, P, and E which are SEQ. ID NOS. 1-5, respectively, for the alpha hemoglobin chain. For the beta hemoglobin chain, bovine, human, porcine, and equine hemoglobin are shown which are SEQ. ID NOS 6-9, respectively.

DETAILED DESCRIPTION OF INVENTION

Figure 2:
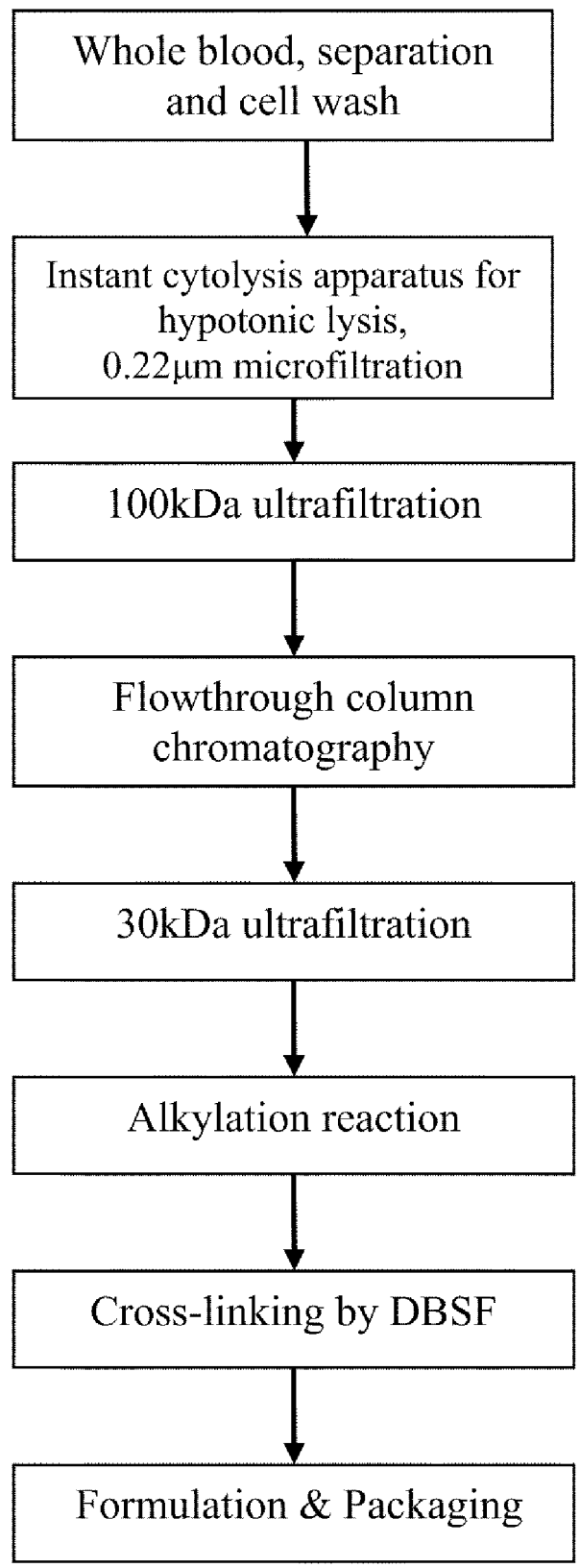
FIG. 2 is a flow-chart depicting an overview of the process of the present invention.

Hemoglobin is an iron-containing oxygen-transport protein in red blood cells of the blood of mammals and other animals. Hemoglobin exhibits characteristics of both the tertiary and quaternary structures of proteins. Most of the amino acids in hemoglobin form alpha helices connected by short non-helical segments. Hydrogen bonds stabilize the helical sections inside the hemoglobin causing attractions within the molecule thereto folding each polypeptide chain into a specific shape. A hemoglobin molecule is an assembly of four globular protein subunits. Each subunit is composed of a polypeptide chain arranged into a set of α-helix structural segments connected in a "myoglobin fold" arrangement with an embedded heme group.

The heme group consists of an iron atom held in a heterocyclic ring, known as a porphyrin. The iron atom binds equally to all four nitrogen atoms in the center of the ring which lie in one plane. Oxygen is then able to bind to the iron center perpendicular to the plane of the porphyrin ring. Thus a single hemoglobin molecule has the capacity to combine with four molecules of oxygen.

In adult humans, the most common type of hemoglobin is a tetramer called hemoglobin A consisting of two α and two β non-covalently bound subunits designated as α2β2, each made of 141 and 146 amino acid residues respectively. The size and structure of α and β subunits are very similar to each other. Each of the subunits has a molecular weight of about 16 kDa for a total molecular weight of the tetramer of about 65 kDa. The four polypeptide chains are bound to each other by salt bridges, hydrogen bonds and hydrophobic interaction. The structure of bovine hemoglobin is similar to human hemoglobin (90.14% identity in α chain; 84.35% identity in β chain). The difference is that the two sulfhydryl groups in the bovine hemoglobin are positioned at β Cys 93, while the sulfhydryls in human hemoglobin are at positioned at α Cys 104, β Cys 93 and β Cys 112 respectively. FIG. 1 shows the amino acid sequences alignment of bovine, human, canine, porcine and equine hemoglobin, respectively labeled B, H, C, P, and E which are SEQ. ID NOS. 1-5, respectively, for the alpha hemoglobin chain. For the beta hemoglobin chain, bovine, human, porcine, and equine hemoglobin are shown which are SEQ. ID NOS 6-9, respectively. The unlike amino acids from various sources are shaded. FIG. 1 indicates that human hemoglobin shares high similarity with bovine, canine, porcine and equine hemoglobin when comparing their amino acid sequences.

In naturally-occurring hemoglobin inside red blood cells, the association of an α chain with its corresponding β chain is very strong and does not disassociate under physiological conditions. However, the association of one αβ dimer with another αβ dimer is fairly weak outside red blood cells. The bond has a tendency to split into two αβ dimers each approximately 32 kDa. These undesired dimers are small enough to be filtered by the kidneys and be excreted, with the result being potential renal injury and substantially decreased intravascular retention time.

Therefore, it is necessary to stabilize any hemoglobin that is used outside of red blood cells both for efficacy and safety. The process for producing the stabilized hemoglobin is outlined below; an overview of the process of the present invention is presented in the flow chart of FIG. 2.

Initially, a whole blood source is selected as a source of hemoglobin from red blood cells. Mammalian whole blood is selected including, but not limited to, human, bovine, porcine, equine, and canine whole blood. The red blood cells are separated from the plasma, filtered, and washed to remove plasma protein impurities.

Figure 3:
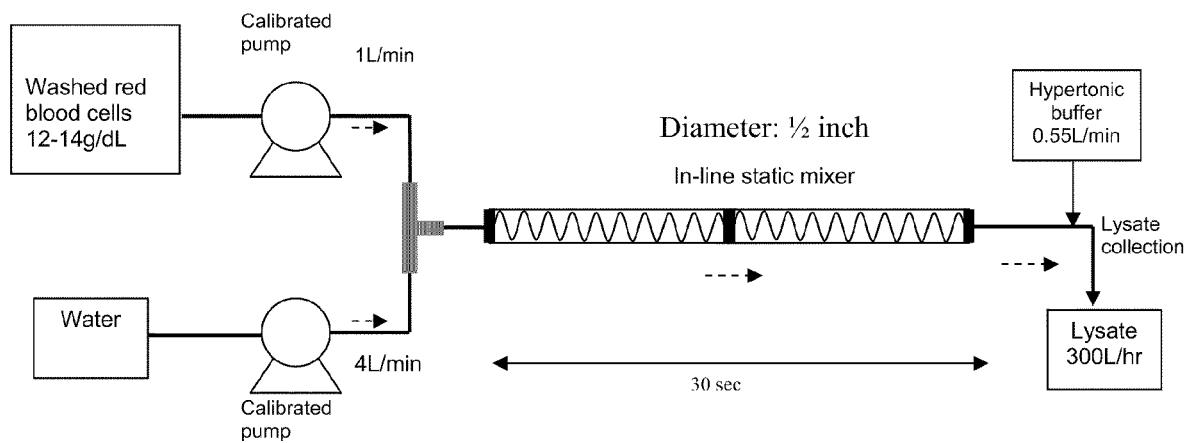
FIG. 3 schematically depicts an instant cytolysis apparatus used in the process of the present invention.

In order to release the hemoglobin from the red blood cells, the cell membrane is lysed. Although various techniques can be used to lyse red blood cells, the present invention uses lysis under hypotonic conditions in a manner which can be precisely controlled at volumes suitable for industrial-scale production. To this end, an instant cytolysis apparatus as seen in FIG. 3 is used to lyse the red blood cells. Hypotonic lysis creates a solution of lysate including hemoglobin and a waste retentate. To enable industrial-scale production, the lysis is carefully controlled such that only red blood cells are lysed without lysing white blood cells or other cells. In one embodiment, the size of the instant cytolysis apparatus is selected such that the red blood cells traverse the apparatus in approximately 30 seconds and the instant cytolysis apparatus includes a static mixer. Deionized and distilled water is used as a hypotonic solution. Of course it is understood that the use of other hypotonic solutions having different saline concentrations would result in different time periods for red blood cell lysis. Because the controlled lysis procedure breaks the red blood cells only, not white blood cells or cellular matter, it minimizes the release of toxic proteins, phospholipids or DNA from white blood cells and other cellular matter. A hypertonic solution is added immediately after 30 seconds, that is, after the red blood-cell containing solution has traversed the static mixer portion of the instant cytolysis apparatus. The resultant hemoglobin has a higher purity and lower levels of contaminants such as undesired DNA and phospholipids than hemoglobin resulted from using other lysis techniques. Undesired nucleic acid from white blood cells and phospholipids impurities are not detected in the hemoglobin solution by polymerase chain reaction (detection limit=64 pg) and HPLC (detection limit=1 μg/mL) method respectively.

Two ultrafiltration processes are performed; one which removes impurities having molecular weights greater than hemoglobin before flowthrough column chromatography, and another which removes impurities having molecular weights less than hemoglobin after flowthrough column chromatography. The latter ultrafiltration process concentrates the hemoglobin. In some embodiments, a 100 kDa filter is used for the first ultrafiltration, while a 30 kDa filter is used for the second ultrafiltration.

Flowthrough column chromatography is used to remove protein impurities in the purified hemoglobin solution such as immunoglobin-G, albumin and carbonic anhydrase. In some embodiments, column chromatography is carried out by using one or a combination of commercially available ion exchange columns such as a DEAE column, CM column, hydroxyapatite column, etc. The pH for column chromatography is typically from 6 to 8.5. In one embodiment, a flowthrough CM column chromatography step is used to remove protein impurities at pH 8.0. Enzyme-linked immunosorbent assay (ELISA) is performed to detect the protein impurities and phospholipids remaining in the sample after elution from the column chromatography. This unique flowthrough column chromatography separation enables a continuous separation scheme enabling industrial-scale production. The ELISA result shows that the amount of these impurities are substantially low in the eluted cross-linked tetrameric hemoglobin (immunoglobin-G: 44.3 ng/mL; albumin: 20.37 ng/mL; carbonic anhydrase: 81.2 μg/mL). The protein impurities removal results using different kinds of column with different pH values are shown in Table 1 below.

TABLE 1

Removal of different protein impurities using different ion-exchange columns

| Column (pH condition) | Removal percentage (%) | | |
|---|---|---|---|
| | Carbonic anhydrase | Albumin | Immunoglobin-G |
| DEAE (at pH 7.5) | — | 68 | 29.8 |
| DEAE (at pH 7.8) | — | 60 | 50.9 |

TABLE 1-continued

Removal of different protein impurities using different ion-exchange columns

| Column (pH condition) | Removal percentage (%) | | |
| --- | --- | --- | --- |
| | Carbonic anhydrase | Albumin | Immunoglobin-G |
| CM (at pH 6.2) | — | 32 | 21.8 |
| CM (at pH 8.0) | 5.6 | 53.2 | 66.4 |
| Hydroxyapatite (at pH 7.5) | 4.5 | 23.5 | 22.8 |

Figure 4:
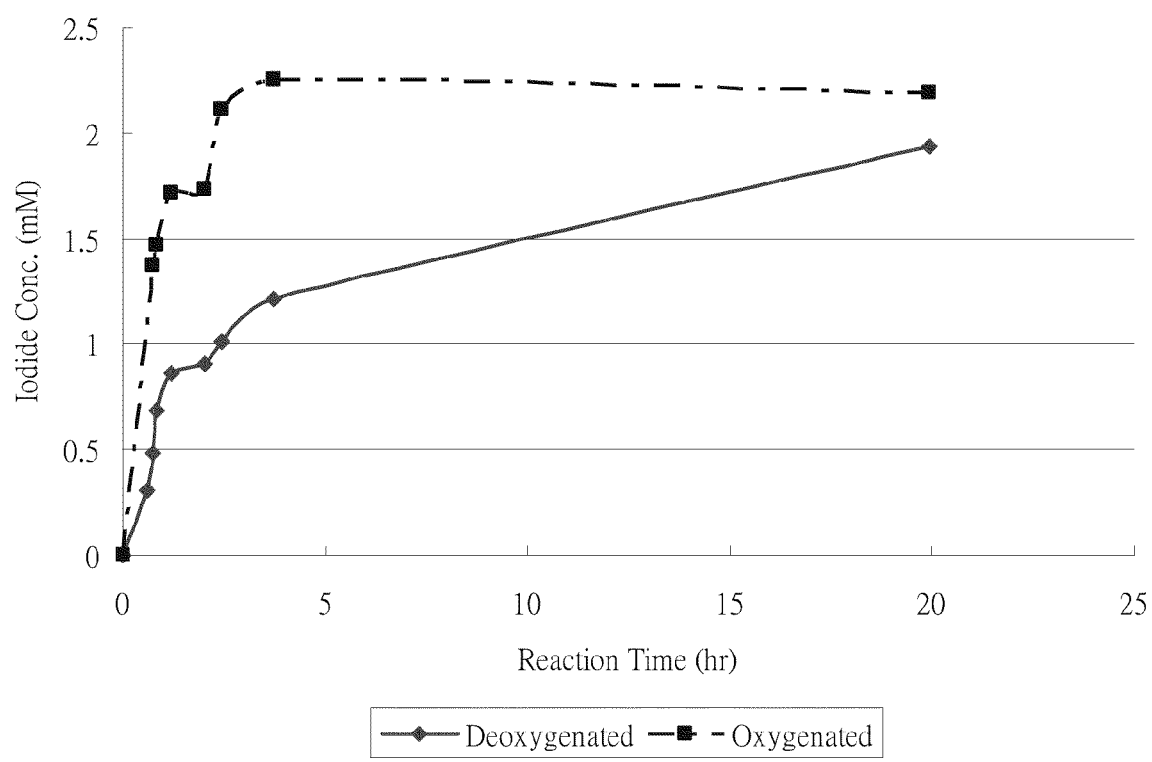
FIG. 4 is a graph showing the reaction of hemoglobin with sulfhydryl reagent in oxygenated and in deoxygenated environments.
Figure 14:
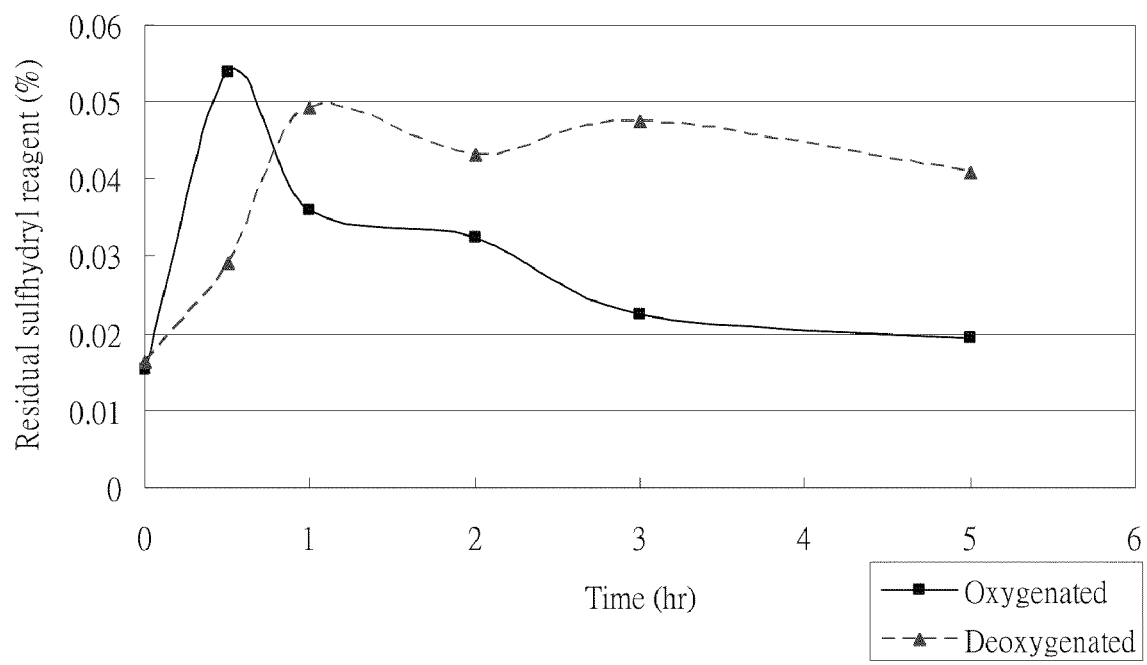
FIG. 14 is a comparison between sulfhydryl reaction in an oxygenated environment and reaction in a deoxygenated environment.

In order to prevent the binding of endothelium-derived relaxing factor to a cysteine site of the hemoglobin causing undesirable vasoconstriction, the hemoglobin is subjected to a reaction with a sulfhydryl reagent under oxygenated conditions. This is in direct contrast to the teachings of the prior art which emphasize reaction between hemoglobin and a sulfhydryl reagent under deoxygenated conditions. The present invention demonstrates that the sulfhydryl reagent reacts faster and in completion with the reactive sulfhydryl groups of hemoglobin under an oxygenated condition. The reaction of sulfhydryl reagent with sulfhydryl groups of hemoglobin produces iodide. Therefore, the completeness of the alkylation reaction can be monitored by measuring the iodide release. During a time-course experiment, the alkylation reaction is performed faster and more efficiently in an oxygenated environment when compared to a deoxygenated environment, as indicated in FIG. 4 and FIG. 14. The reaction time required to reach completion is reduced to under 5 hours in an oxygenated environment when compared to a deoxygenated environment. A shorter reaction time is very important for an industrial-scale process. It also reduces reactions caused by unwanted impurities that lead to adverse effects in the final product.

Following the sulfhydryl reaction process, the hemoglobin is subjected to α-α and/or β-β cross-linking by bis-3,5-dibromosalicy fumarate (DBSF). In order to prevent formation of polymeric hemoglobin, the reaction is carefully controlled in a deoxygenated environment with a molar ratio of hemoglobin to DBSF between 1:2.5 to 1:4.0 such that the resultant α-α and/or β-β cross-linked hemoglobin is tetrameric hemoglobin having a molecular weight of 60-70 kDa, demonstrating that polymeric hemoglobin is not present. The yield of the DBSF reaction is high, >99% and the dimer concentration in the final product is low; in the context of this invention, low dimer content means less than 5% and, more preferably, less than 2% dimer. In one embodiment, the cross-linking is selected such that the β-β cross-linked hemoglobin is greater than 50% of the total cross-linked tetrameric hemoglobin. In another embodiment, the cross-linking is selected such that the β-β cross-linked hemoglobin is 60% or greater of the total. Further, conditions can be selected such that the β-β cross-linked hemoglobin is greater than 70% of the total tetrameric hemoglobin. There is some evidence that β-β cross-linked hemoglobin may have a lower oxygen affinity than α-α cross-linked tetrameric hemoglobin. Therefore, there may be situations in which a higher percentage of β-β cross-linked hemoglobin is preferred to α-α cross-linked hemoglobin to enhance the efficiency of oxygen transport. Further, β-β cross-linked hemoglobin may result in fewer α-β dimers which would assist in reducing renal toxicity.

N-acetyl cysteine is added at a concentration of 0.2-0.4% to the α-α and/or β-β cross-linked tetrameric hemoglobin to maintain a level of met-hemoglobin below 5%.

Depending upon the final application of the hemoglobin, the purified, cross-linked tetrameric hemoglobin of the present invention is optionally packaged in an air-tight package in a deoxygenated environment. The packaging used in the present invention results in the α-α and/or β-β cross-linked tetrameric hemoglobin being stable for more than two years. In contrast, the hemoglobin of the present invention converts into inactive met-hemoglobin rapidly within few days under oxygenated conditions. Prior art hemoglobin solutions have been packaged in PVC or Stericon blood bags which have high oxygen permeability, thus shortening the life span of the product.

In many embodiments of the present invention, the oxygen-carrier-containing cross-linked hemoglobin-containing pharmaceutical composition is delivered by intravenous injection. Therefore, the packaging design and material choice are directed towards intravenous injection applications. A multi-layer package of EVA/EVOH material is used to minimize the gas permeability and to avoid the formation of inactive met-hemoglobin. A 100 mL infusion bag designed for use with the purified and cross-linked hemoglobin of the present invention is made from a five layers EVA/EVOH laminated material with a thickness of 0.4 mm that has an oxygen permeability of 0.006-0.132 $cm^3$ per 100 square inches per 24 hours per atmosphere at room temperature. This material is a Class VI plastic (as defined in USP<88>), which meets the in-vivo Biological Reactivity Tests and the Physico-Chemical Test and is suitable for fabricating an infusion bag for intravenous injection purpose. This primary bag is particular useful to protect the α-α and/or β-β cross-linked tetrameric hemoglobin solution from long term oxygen exposure that cause its instability and eventually affects its therapeutic properties.

For secondary protection of blood products, it has been known to use aluminum overwrap to protect against potential air leakage and to maintain the product in a deoxygenated state. However, there is a potential of pin holes in the aluminum overwrap that compromise its air tightness and make the product unstable. Therefore the present invention uses as secondary packaging an aluminum overwrap pouch which prevents oxygenation and also prevents light exposure. The composition of the overwrap pouch includes 0.012 mm of polyethylene terephthalate (PET), 0.007 mm of aluminum (AL), 0.015 mm of nylon (NY) and 0.1 mm of polyethylene (PE). The overwrap film has a thickness of 0.14 mm and an oxygen transmission rate of 0.006 $cm^3$ per 100 square inches per 24 hours per atmosphere at room temperature. This secondary packaging lengthens the stability time for the hemoglobin, extending the product shelf-life.

Figure 5:
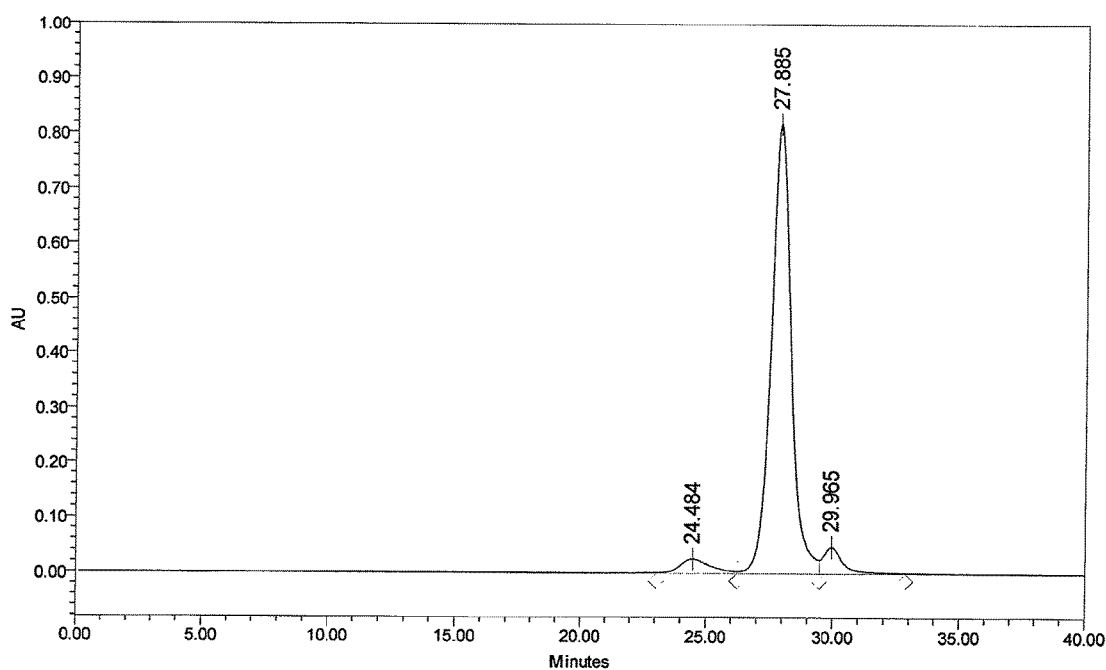
FIG. 5 depicts high performance liquid chromatography analysis for cross-linked tetrameric hemoglobin.

High performance liquid chromatography (HPLC), electrospray ionization mass spectrometry (ESI-MS), and circular dichroism (CD) spectroscopy are used to analyze and characterize the α-α and/or β-β cross-linked tetrameric hemoglobin. For a bovine blood source, FIG. 5 shows the composition of the product in terms of molecular weight distribution by HPLC analysis. An HPLC analytical method is used to detect the amount of tetramer and dimer respectively. The mobile phase for HPLC analysis contains magnesium chloride (0.75M) which can separate dimer, uncross-linked tetramer, and stabilized α-α and/or β-β cross-linked tetramer. For promoting hemoglobin dissociation into dimers, magnesium chloride is approximately 30 times more effective than sodium chloride at the same ionic strength.

Figure 6:
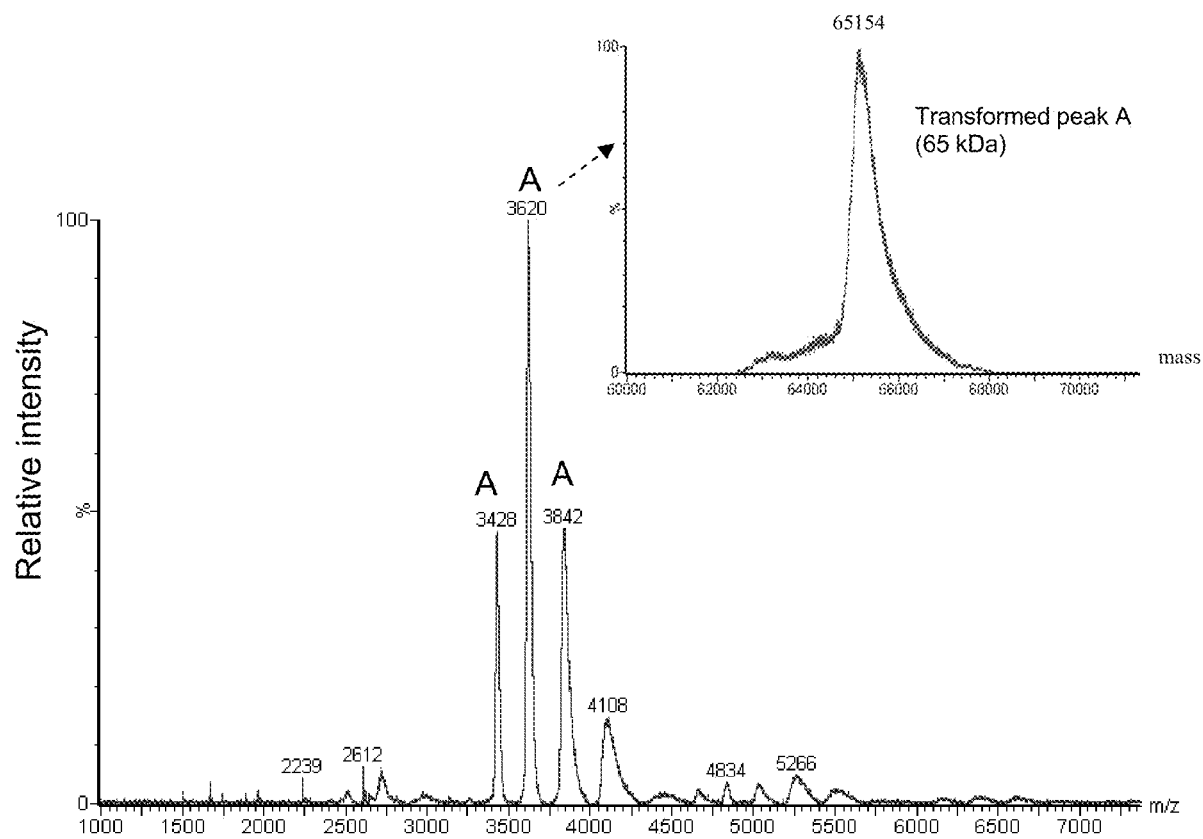
FIG. 6 depicts electrospray ionization mass spectrometry (ESI-MS) analysis for the cross-linked tetrameric hemoglobin.
Figure 7:
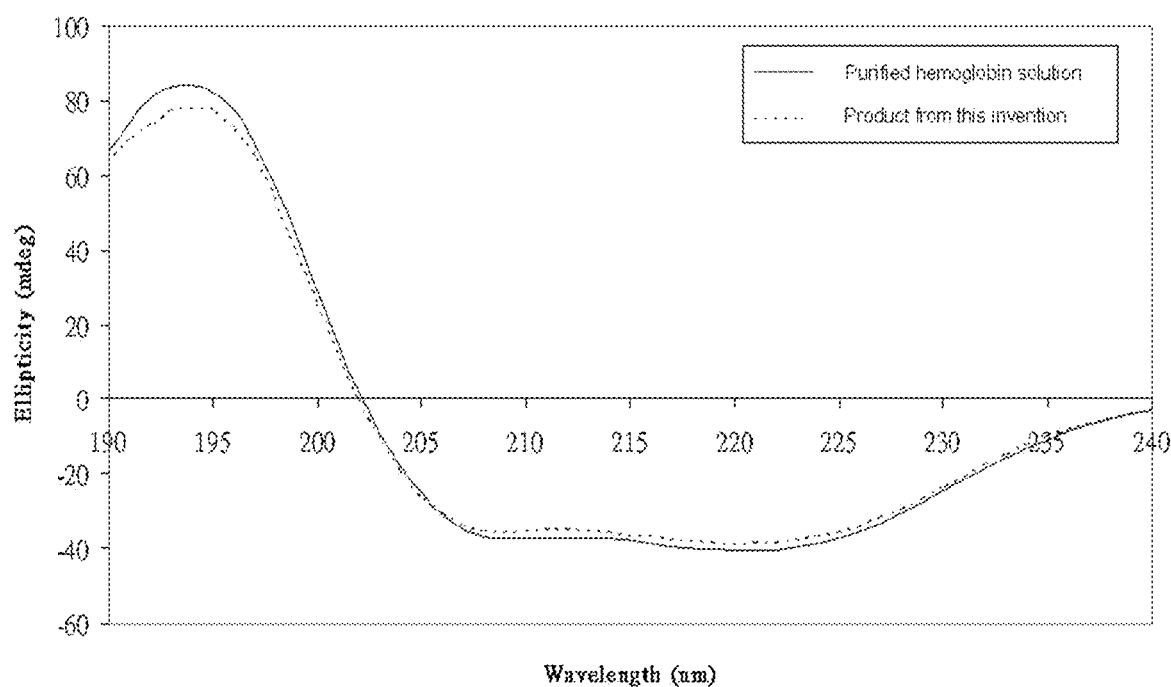
FIG. 7 shows a circular dichroism (CD) spectroscopy analysis for (a) purified hemoglobin solution and (b) cross-linked tetrameric hemoglobin.

ESI-MS allows the analysis of very large molecules. It is an ionization technique that analyzes the high molecular weight compound by ionizing the protein, and then separating the ionized protein based on mass/charge ratio. Therefore, the molecular weight and the protein interactions can be determined accurately. In FIG. 6, ESI-MS analysis result indicates that the size of stabilized tetramer is 65 kDa. The far UV CD spectra from 190 to 240 nm reveal the secondary structures of globin portion of the hemoglobin. In FIG. 7, the consistency of the spectra of the purified and cross-linked hemoglobin reveals that the hemoglobin chains are properly folded even after the cross-linking by DBSF. The CD result shows that the cross-linked hemoglobin has around 42% of alpha-helix, 38% of beta-sheet, 2.5% of beta-turn and 16% of random coil. It further confirms that cross-linking step with DBSF to form cross-linked tetrameric hemoglobin does not affect the secondary structure of hemoglobin.

The purified cross-linked tetrameric hemoglobin produced by the process of the present invention has a molecular weight of 60-70 kDa and has at least one cysteine moiety wherein said cysteine moiety includes a thiol-protecting group such that the hemoglobin is incapable of binding endothelium-derived relaxing factor at the cysteine site. Further, the cross-linked tetrameric hemoglobin is non-pyrogenic, endotoxin free (<0.05 EU/mL), and stroma free (<1%).

The process of the present invention is applicable to large-scale industrial production of cross-linked tetrameric hemoglobin. In addition, the cross-linked tetrameric hemoglobin in combination with a pharmaceutical carrier (e.g. water, physiological buffer, in capsule) is suitable for mammalian use.

The cross-linked tetrameric hemoglobin of the present invention is used for tissue oxygenation, for cancer treatment, for the treatment of an oxygen-deprivation disorder such as hemorrhagic shock, and in heart preservation under a low oxygen content environment (e.g. heart transplant). The dosage of cross-linked tetrameric hemoglobin is selected at a concentration range of approximately 0.3-1.3 g/kg.

For use in cancer treatment, the oxygen-carrier-containing pharmaceutical composition of the present invention serves as a tissue oxygenation agent to improve the oxygenation in tumor tissues, thereby enhancing chemo-sensitivity (e.g., sensitivity to chemotherapy) and radiation sensitivity.

Figure 8:
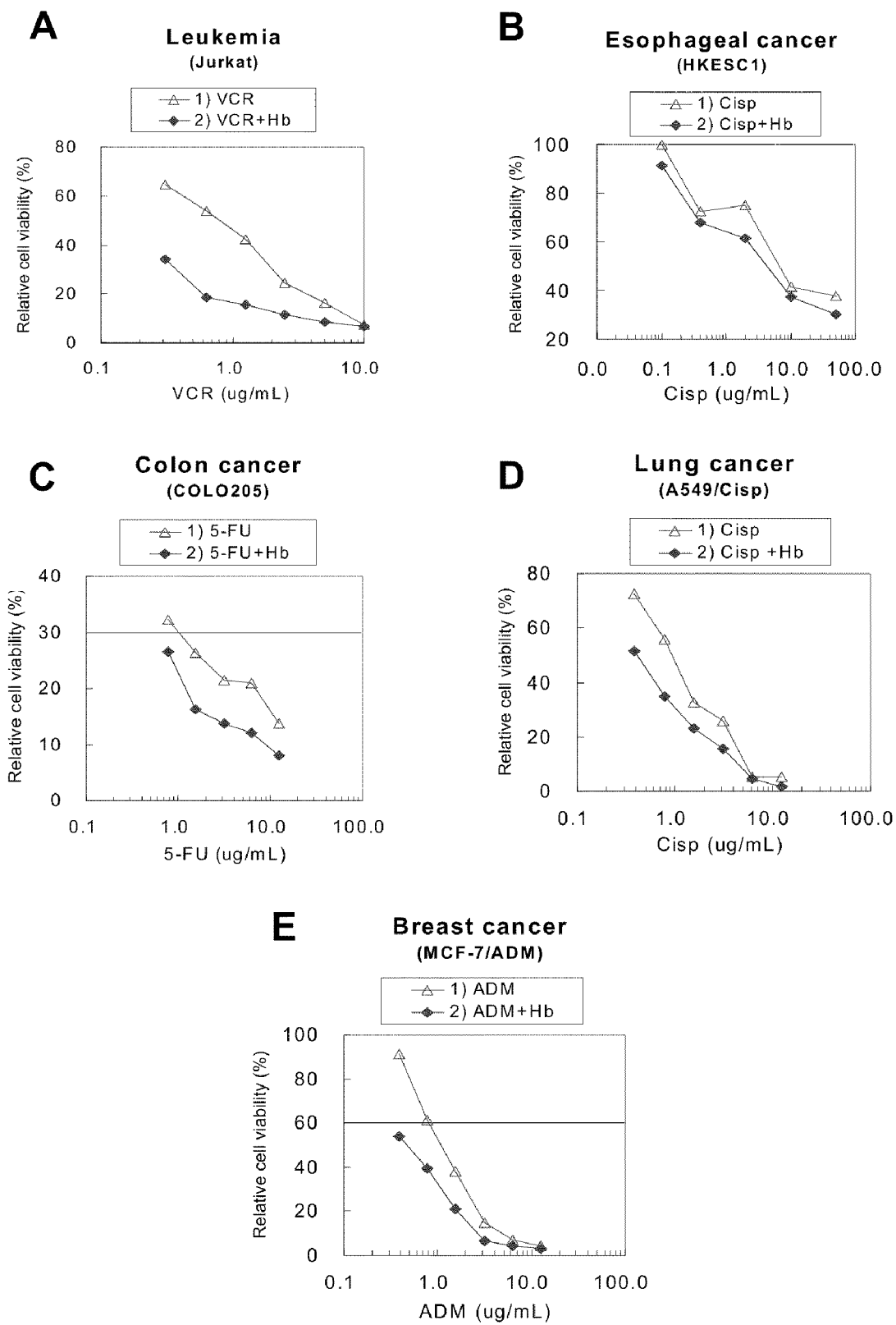
FIG. 8 shows the chemo-sensitization effects of cross-linked tetrameric hemoglobin in vitro.

FIG. 8 demonstrates the enhanced chemo-sensitivity of cancer tumor cells after applying a composition including cross-linked tetrameric hemoglobin in vitro. Five different cancer cell lines (A) Jurkat (leukemia), (B) HKESC1 (Esophageal cancer), (C) COL0205 (Colon cancer), (D) A549/Cisp (Lung cancer) and (E) MCF-7/ADM (Breast cancer) are treated with various chemotherapeutic agents alone, or in combination with the cross-linked tetrameric hemoglobin of the present invention. Inhibition of tumor cell growth is determined by the ATP tumor chemo-sensitivity assay (ATP-TCA) (for Jurkat, COL0205, A549/Cisp, and MCF-7/ADM cell lines) or MTT cell proliferation assay (for HKESC1 cell line). The results show that the chemo-sensitivity is highly enhanced by addition of the inventive cross-linked tetrameric hemoglobin in all cancer cell lines including two cell lines, A549/Cisp and MCF-7/ADM, which are highly resistant to chemotherapy. The results in FIG. 8 show that as a result of the enhanced chemo-sensitivity by addition of the cross-linked tetrameric hemoglobin, the treatment efficacy for leukemia cells, esophageal cancer cells, lung cancer cells, colon cancer cells, and breast cancer cells is greatly increased.

In addition, the ability of the inventive cross-linked tetrameric hemoglobin to improve oxygenation in normal tissues (FIG. 9) and in extremely hypoxic tumor tissue (FIG. 10) (human nasopharyngeal carcinoma (CNE2)), is demonstrated in this invention. The representative oxygen profile along the tissue track of a human CNE2 xenograft is showed in FIG. 10. Oxygen partial pressure within the tumor mass is directly monitored by a fiber-optic oxygen sensor (Oxford Optronix Limited) coupled with a micro-positioning system (DTI Limited). After intravenous injection of 1.2 g/kg of the cross-linked tetrameric hemoglobin, the median pO2 value rises from 0.2 mmHg to 3.9 mmHg in 3 hours and 10.6 mmHg in 6 hours respectively. Even in the most hypoxic regions, the oxygen carrier-containing pharmaceutical composition of the present invention significantly increased oxygen tension. No other similar commercial products or any existing technologies show as high an efficacy when compared to the oxygen-carrier-containing pharmaceutical composition prepared in this invention.

For the use in the treatment of oxygen-deprivation disorder and in heart preservation, the oxygen-carrier-containing pharmaceutical composition of the present invention serves as a blood substitute providing oxygen to a target organ. In some embodiments, the composition is used as a cardioplegic solution for heart preservation.

Figure 11:
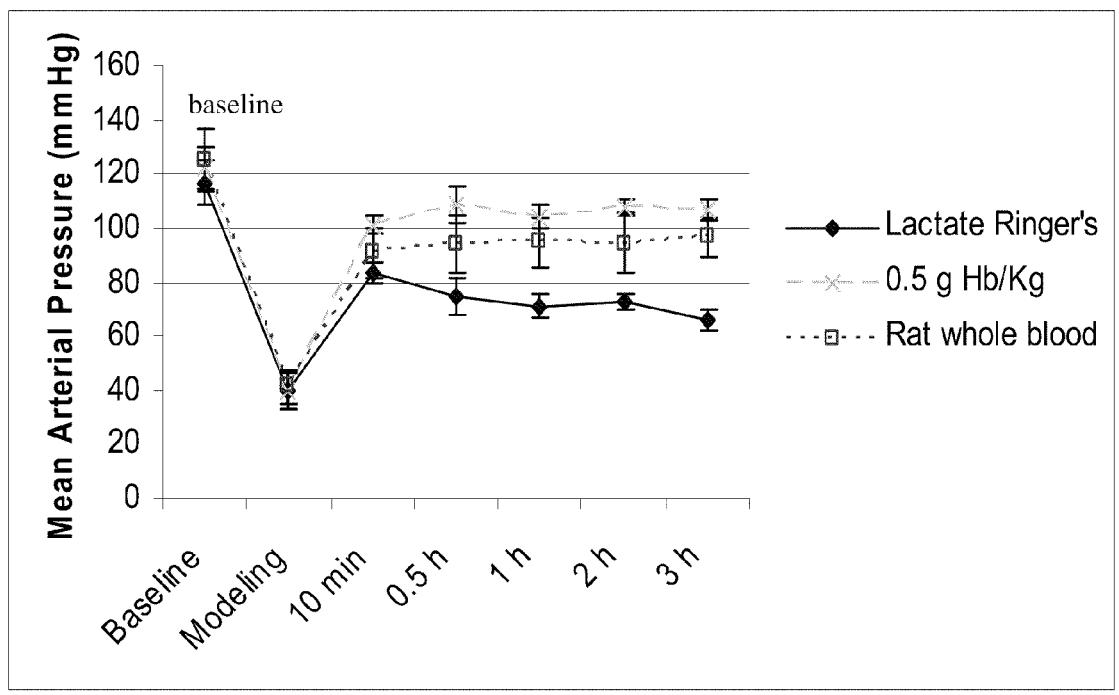
FIG. 11 shows the mean arterial pressure changes in a rat model of severe hemorrhagic shock after the treatment with the stabilized cross-linked tetrameric hemoglobin of the present invention.

The mean arterial pressure changes in a rat model of severe hemorrhagic shock (see Example 12b) after the treatment with 0.5 g/kg of the cross-linked tetrameric hemoglobin of the present invention are showed in FIG. 11. In a rat model of severe hemorrhagic shock, the mean arterial pressure is returned back to a safe and stable level and maintained below the baseline after treatment with the stabilized cross-linked tetrameric hemoglobin. Following treatment with the hemoglobin of the present invention, the reaction time for the mean arterial pressure to return to normal is even shorter than that following administration of rat whole blood which serves as a positive control. The above results indicate that the vasoactive event after the transfusion of the inventive hemoglobin is beneficial to maintain a stable and hemodynamic state. Prior hemoglobin-based oxygen carriers caused many vasoconstriction events. For example, the Hemopure® product (Biopure Co., USA) resulted in higher mean arterial pressure (124±9 mmHg) when compared to the baseline (96±10 mmHg) as disclosed by Katz et al., 2010.

Use of the inventive hemoglobin for infusion increases the survival rate in a shock model in mouse (from 18% to 75%) and beagle dogs (from 46% to 97%). The survival rate of a severe hemorrhagic shock animal model is significantly increased by infusing different amounts of the cross-linked tetrameric hemoglobin (see Example 12). Thus the inventive hemoglobin is used as a treatment for hemorrhagic shock.

EXAMPLES

The following examples are provided by way of describing specific embodiments of the invention without intending to limit the scope of the invention in any way.

Example 1

Overall Process

A schematic flow diagram of the process of the present invention is illustrated in FIG. 2. Bovine whole blood is collected into an enclosed sterile container/bag containing 3.8% (w/v) tri-sodium citrate solution as anti-coagulant. Blood is then immediately mixed well with tri-sodium citrate solution to inhibit blood clots. Red blood cells (RBC) are isolated and collected from plasma and other smaller blood cells by an apheresis mechanism. A "cell washer" is used for this procedure with gamma sterilized disposable centrifuge bowl. RBC are washed with an equal volume of 0.9% (w/v sodium chloride) saline.

Washed RBC are lysed to release hemoglobin content by manipulating hypotonic shock to the RBC cell membrane. A specialized instant cytolysis apparatus for RBC lysis device depicted in FIG. 3 is used for this purpose. Following RBC lysis, hemoglobin molecules are isolated from other proteins by tangential-flow ultrafiltration using 100 kDa membrane. Hemoglobin in the filtrate is collected for flowthrough column chromatography and further concentrated to 12-14 g/dL by a 30 kDa membrane. Column chromatography is carried out to remove the protein impurities.

The concentrated hemoglobin solution is first modified by a sulfhydryl reagent (alkylation reaction) under natural oxygenated condition, then the components are reacted with DBSF to form stable α-α and/or β-β cross-linked tetrameric hemoglobin molecules.

Example 2

Time & Controlled Hypotonic Lysis and Filtration

Bovine whole blood is freshly collected and transported under a cool condition. The red blood cells are separated from the plasma via a cell washer and subsequently with a 0.65 μm filtration. After washing the red blood cells (RBC) filtrate with 0.9% saline, the filtrate is disrupted by hypotonic lysis. The hypotonic lysis is performed by using the instant cytolysis apparatus depicted in FIG. 3. The instant cytolysis apparatus includes a static mixer to assist in cell lysis. A RBC suspension with controlled hemoglobin concentration (12-14 g/dL) is mixed with 4 volumes of purified water to generate a hypotonic shock to RBC cell membranes. The period of hypotonic shock is controlled to avoid unwanted lysis of white blood cells and platelets. The hypotonic solution passes through the static mixer portion of the instant cytolysis apparatus for approximately 30 seconds. The shock is terminated after 30 seconds by mixing the lysate with 1/10 volume of hypertonic buffer as it exits the static mixer. The hypertonic solution used is 0.1M phosphate buffer, 7.4% NaCl, pH 7.4. The instant cytolysis apparatus of FIG. 3 can process at 50 to 1000 liters of lysate per hour and, preferably at least 300 liters per hour in a continuous manner.

Following the RBC lysis, the lysate of red blood cells is filtered by a 0.22 μm filter to obtain a hemoglobin solution. Nucleic acid from white blood cells and phospholipids impurities are not detected in the hemoglobin solution by polymerase chain reaction (detection limit=64 pg) and HPLC (detection limit=1 μg/mL) method respectively. A first 100 kDa ultrafiltration is performed to remove impurities having a higher molecular weight than hemoglobin. A flowthrough column chromatography is followed to further purify the hemoglobin solution. A second 30 kDa ultrafiltration is then performed to remove impurities having a lower molecular weight than hemoglobin and for concentration.

Example 3

Viral Clearance Study on Stroma-Free Hemoglobin Solution

In order to demonstrate the safety of the product from this invention, the virus removal abilities of (1) 0.65 μm diafiltration step and (2) 100 kDa ultrafiltration step are demonstrated by virus validation study. This is done by the deliberate spiking of a down-scaled version of these two processes with different model viruses (encephalomyocarditis virus, pseudorabies virus, bovine viral diarrhoea virus and bovine parvovirus). In this study, four types of viruses (see the following table 2) were used. These viruses vary in their biophysical and structural features and they display a variation in resistance to physical and chemical agents or treatments.

TABLE 2

| Target Virus | Model Virus | Taxonomy | Genome | Structure | Size [nm] | Stability* |
|---|---|---|---|---|---|---|
| Hepatitis C virus (HCV) | Bovine viral diarrhea virus (BVDV) | Flaviviridae | ssRNA | enveloped | 40-60 | low |
| — | Encephalomyocarditis virus (EMCV) | Picornavirus | ssRNA | non-enveloped | 25-30 | medium |
| Parvovirus B19 | Bovine parvovirus (BPV) | Parvoviridae | ssDNA | non-enveloped | 18-26 | very high |
| Hepatitis B virus (HBV) | Bovine parvovirus (PRV) | Herpesviridae | dsDNA | enveloped | 120-200 | Low to medium |

The virus validation scheme is briefly shown in the following table 3.

TABLE 3

| Diafiltration | Ultrafiltration |
|---|---|
| Cell Washing | Virus spiking |
| ↓ | ↓ |
| Virus spiking | Ultrafiltration |
| ↓ | ↓ |
| Diafiltration | Virus tests |
| ↓ | |
| Virus tests | |

The summary of the log reduction results of the 4 viruses in (1) 0.65 µm diafiltration and (2) 100 kDa ultrafiltration is shown below in Table 4. All four viruses, BVDV, BPV, EMCV and PRV, were effectively removed by 0.65 µm diafiltration and 100 kDa ultrafiltration.

TABLE 4

| Viruses | BVDV | | BPV | | EMCV | | PRV | |
|---|---|---|---|---|---|---|---|---|
| Run | 1 | 2 | 1 | 2 | 1 | 2 | 1 | 2 |
| 0.65 µm Diafiltration | 2.69 | 3.20 | 3.73 | 3.53 | 3.25 | ≧3.90 | 2.67 | 2.63 |
| 100 kDa Ultrafiltration | ≧4.68 | ≧4.38 | 5.87 | 5.92 | 3.60 | 3.43 | ≧6.05 | 3.27 |
| Cumulative maximum | ≧7.88 | | 9.65 | | ≧7.50 | | ≧8.72 | |
| Cumulative minimum | ≧7.07 | | 9.40 | | 6.68 | | 5.90 | |

Annotation
≧ no residual infectivity determined

Example 4

Flowthrough Column Chromatography

Figure 12:
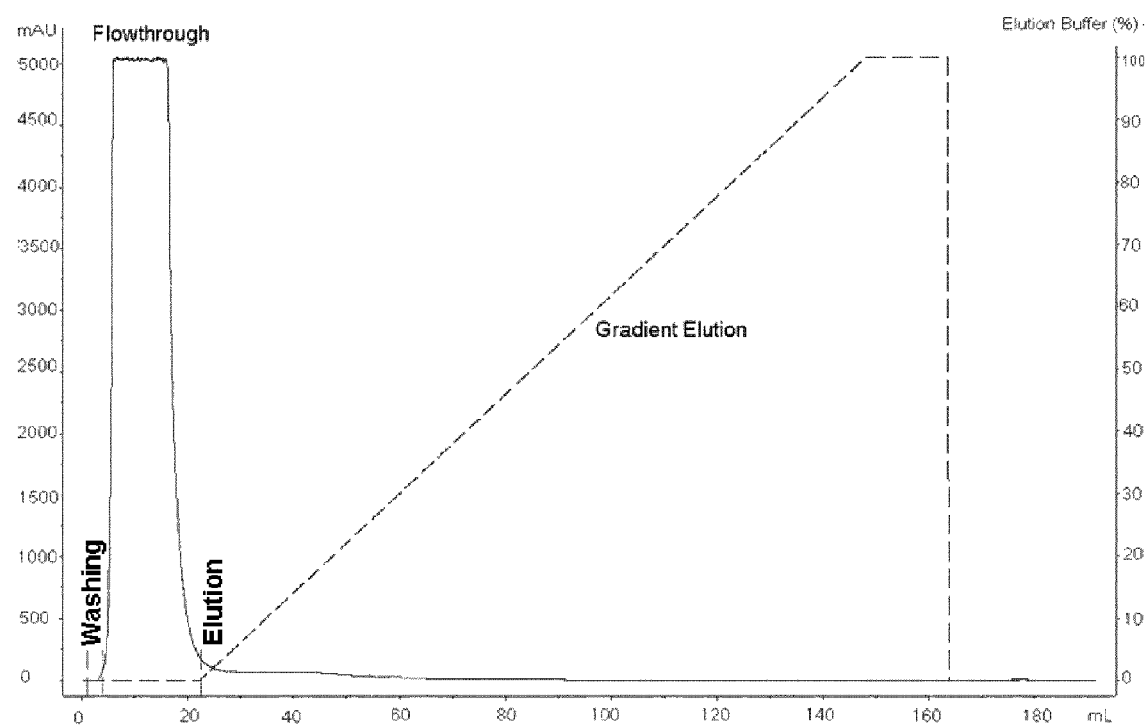
FIG. 12 is an elution profile for flowthrough column chromatography; the hemoglobin solution is in the flowthrough fraction.

A CM column (commercially available from GE healthcare) is used to further remove any protein impurities. The starting buffer is 20 mM sodium acetate (pH 8.0), and the elution buffer is 20 mM sodium acetate, 2M NaCl (pH 8.0). After the equilibration of the CM column with starting buffer, the protein sample is loaded into the column. The unbound protein impurities are washed with at least 5 column volume of starting buffer. The elution is performed using 25% elution buffer (0-0.5M NaCl) in 8 column volume. The elution profile is shown in FIG. 12; the hemoglobin solution is in the flowthrough fraction.

The purity of flowthrough fraction is analyzed by ELISA. The results are indicated in the following table 5.

TABLE 5

| | Protein impurities | | |
|---|---|---|---|
| | Immunoglobin-G | Carbonic anhydrase | Albumin |
| Before CM column | 1320 ng/mL | 860.3 µg/mL | 435.2 ng/mL |
| Flowthrough (containing hemoglobin) | 44.3 ng/mL | 81.2 µg/mL | 20.4 ng/mL |

Figure 13:
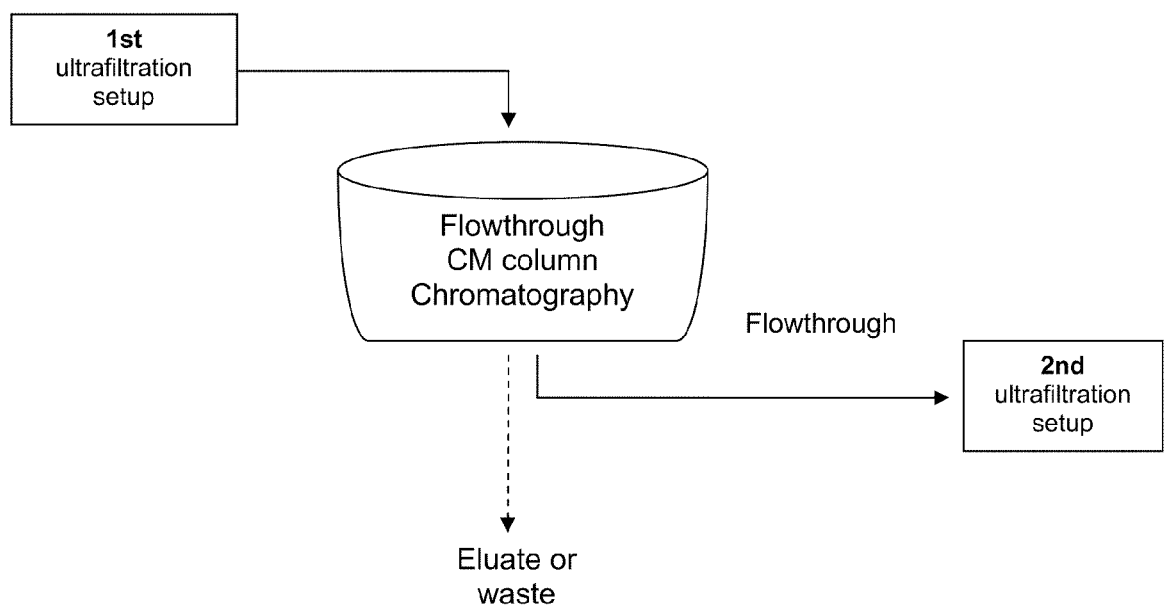
FIG. 13 schematically depicts a flowthrough CM column chromatography system with ultrafiltration for an industrial scale operation.

As the hemoglobin solution is in the flowthrough from the CM column chromatography at pH 8 (not in the eluate), it is a good approach for continuous industrial scale operation. The first ultrafiltration set-up is connected directly to the flowthrough CM column chromatography system, and the flowthrough tubing can connect to the second ultrafiltration set-up for industrial scale operation. The schematic industrial process configuration is shown in FIG. 13.

Example 5

Sulfhydryl Reaction and Cross-Linking (5a) Sulfhydryl Reaction

In the present invention, reaction between hemoglobin and sulfhydryl is performed in an oxygenated environment in contrast to the teachings of the prior art, in which the reaction typically takes place in an inert atmosphere such as nitrogen. An alkylating sulfhydryl reagent is added to alkylate the free sulfhydryl groups of hemoglobin. In this embodiment, the molar ratio of hemoglobin to sulfhydryl reagent is 1:2 to 1:4. This reaction can eliminate the binding of endothelium-derived relaxing factor which reacts with hemoglobin sulfhydryl groups. Endothelium-derived relaxing factor has been demonstrated to bind to the reactive sulfhydryl groups of hemoglobin, which may account for the increase of blood pressure observed after the infusion of earlier generations of hemoglobin-based oxygen carriers. The completion of the sulfhydryl reaction can be monitored by measuring the release of product or the residual sulfhydryl reagent (by UV spectrometry, at 265 nm). FIG. 14 is a comparison between reaction in an oxygenated environment and reaction in a deoxygenated environment. FIG. 14 shows that the residual sulfhydryl reagent levels off at 3 hours in an oxygenated environment during a time-course experiment. In contrast, a lot of unreacted sulfhydryl reagent remains in a deoxygenated environment. The yield of the sulfhydryl reaction in an oxygenated environment is high (92.7%) after 4 hours of reaction.

(5b) Cross-Linking Reaction to Form Stable Tetramers

The α-α and/or β-β cross-linking reaction is carried out in a deoxygenated environment. Bis-3,5-dibromosalicyl fumarate (DBSF) is added to the hemoglobin solution to form cross-linked tetrameric hemoglobin that includes α-α cross-linking and/or β-β cross-linking within the tetramer. Optionally, some α-β cross-linking is included within the tetramer.

In this embodiment, the molar ratio of hemoglobin and DBSF is between 1:2.5 to 1:4.0. The DBSF stabilization procedure stabilizes the tetrameric form of hemoglobin (65 kDa) and prevents dissociation into dimers (32 kDa) which are excreted through the kidneys. In this cross-linking process, only tetrameric hemoglobin is formed; no polymeric hemoglobin is formed. This process is carried out in an inert atmosphere of nitrogen to prevent oxidation of the hemoglobin to form ferric met-hemoglobin which is physiologically inactive. The completeness of DBSF reaction is monitored by measuring the residual DBSF using HPLC. The yield of DBSF reaction is high, >99%.

In one embodiment, the cross-linking reaction is carried out in a deoxygenated environment (dissolved oxygen <0.1 mg/L) at room temperature (15-25° C.). DBSF is added to the hemoglobin solution to form cross-linked tetrameric hemoglobin; this cross-linked tetrameric hemoglobin is characterized as set forth below. Note that this characterization is based on one embodiment only. The various proportions and types of cross-links within the tetramer can be controlled by the amount of DBSF used, the time and temperature of the reaction, and other process conditions.

When changing the molar ratio of hemoglobin and DBSF to 1:5.0, the percentage of octamer (130 kDa) is sharply increased to 18%.

(5b-1) Electrophoretic Analysis on Cross-Linked Hemoglobin Using 15% SDS-PAGE

Cross-linked hemoglobin solution was mixed with an equal volume of reducing sample buffer (62 mM Tris-HCl (pH 6.8), 10% (v/v) glycerol, 5% (v/v) mercaptoethanol and 2.3% (w/v) SDS), and heated at 95° C. for 10 min. The sample mixtures were resolved using a 15% acrylamide slab gel with a 4% stacking gel. The electrophoresis was run with a constant current of 60 mA. After electrophoresis, the SDS-PAGE gel was stained with 0.1% (w/v) Coomassie blue R350, 20% (v/v) methanol, and 10% (v/v) acetic acid. The intensities of protein bands expressed in Black Light Unit (BLU) were quantified using Bio-Rad Quantity One Software.

(5b-2) Trypsin Digestion of Protein Bands Excised from 15% SDS-PAGE

Protein bands were excised from the SDS-PAGE gel, cut into cubes (1×1 mm), destained with 10% methanol/10% acetic acid. The destained gel were reduced with 10 mM DTT in 25 mM $NH_4CO_3$ and alkylated with 55 mM idoacetamide in 25 mM $NH_4CO_3$ for 45 min in dark, and then in-gel digested with 20 ng/μL modified trypsin in 25 mM $NH_4CO_3$ at 37° C. overnight. After trypsin digestion, the trypsin-digested peptides were extracted by diffusion into 50% (v/v) acetonitrile and 1% (v/v) trifluoroacetic acid (TFA).

(5b-3) Matrix-Assisted Laser Dissociation/Ionization—Time of Flight Mass Spectrometry (MALDI-TOF MS) Analysis of Trypsin-Digested Protein Bands The trypsin digested peptides extracted from the gel cubes were spotted onto Anchorchip plate, which was pre-spotted with 1 μL of matrix solution (2 mg/mL HCCA, saturated in 50% acetonitrile/0.1% TFA, and allowed to air-dry. After drying, the sample spot was washed with 10 mM monophosphate buffer and recrystallized using a solution of EtOH:acetone:0.1% TFA (6:3:1 ratio). MALDI-TOF MS analysis was performed with a Bruker Autoflex III (Bruker Daltonic GmbH, Bremen, Germany) operated in the reflectron mode over the m/z range of 800-3500 Da and the parameters were set as follows: ion source 25 kV for peptide mass fingerprint (PMF), and reflector 26.3 kV for PMF. External calibration was performed using Bruker Peptide Mix Calibration Standard. The peaks with ratio of S/N over 4 were automatically labelled by Flex-Analysis (Bruker Daltonic GmbH, Bremen, Germany). The MS data was further analyzed through MASCOT 2.2.04 and Biotools 2.1 softwares (Bruker Daltonic GmbH, Bremen, Germany), and these data were searched against Mammalian proteins in NCBI nonredundant (NCBInr) database. The following parameters were used for database searches: monoisotopic mass accuracy <250 ppm, parent charge +1, missed cleavages 1, carbamidomethylation of cysteine as fixed modification, oxidation of methionine as variable modification. The results with protein score more than 67 (p=0.05) based on PMF was considered as positive identification. Other criteria for confident identification were that the protein match should have at least 15% sequence coverage and match at least 4 peptides.

After combination the analysis results from (a) 15% SDS-PAGE and (b) MALDI-TOF MS, the composition of cross-linked hemoglobin is determined. From the results, 70% of cross-linked hemoglobin is β-β linked.

Example 6

Maintaining a Low Level of Inactive Met-Hemoglobin in the Product after Formulation When compared to other oxygen carrier pharmaceutical products or a product formed in accordance with the methods disclosed in U.S. Pat. No. 7,494,974 B2 and U.S. Pat. No. 7,504,377 B2, the product from this invention contains low levels of inactive met-hemoglobin molecules. In this embodiment, an anti-oxidant such as N-acetyl cysteine is added at 0.2% to the cross-linked tetrameric hemoglobin. Without adding the anti-oxidant, inactive met-hemoglobin is found at a high level (12-20%). The product from this invention has a low level of inactive met-hemoglobin (<5%) and it is high-temperature stable resulting in greater efficacy when used in treatment.

Figure 15:
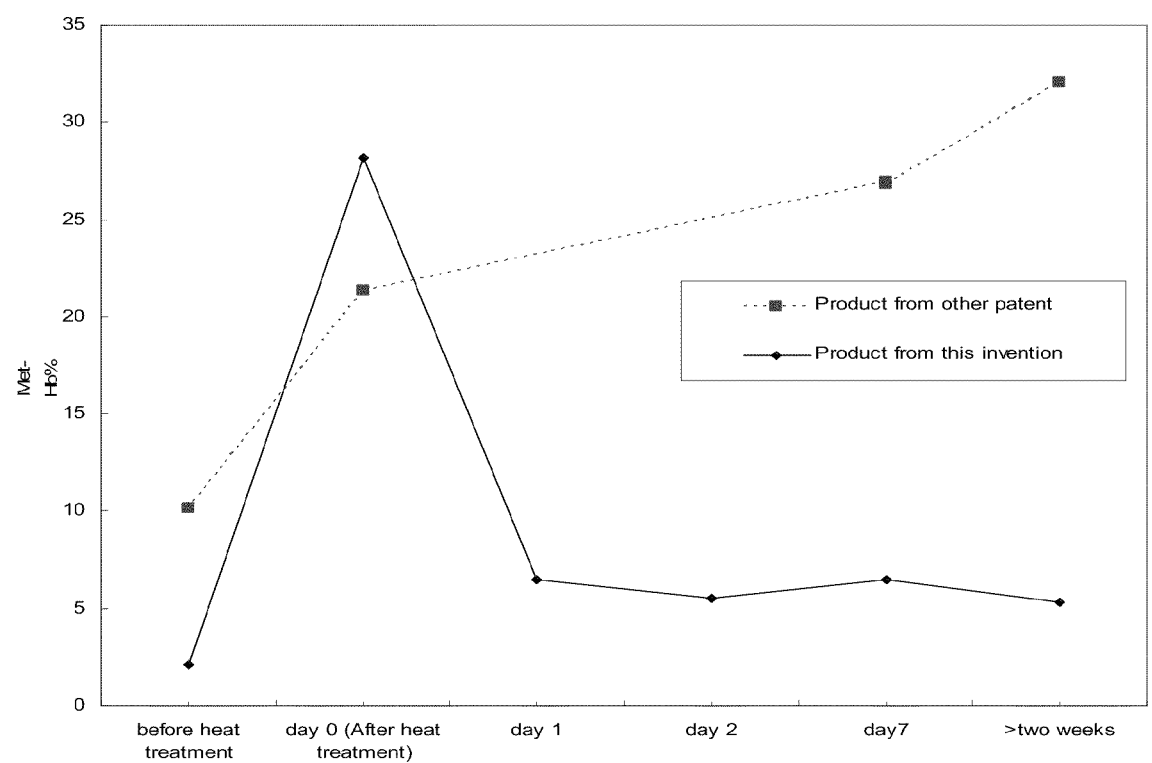
FIG. 15 is a graph demonstrating the heat stability of the cross-linked tetrameric hemoglobin of the present invention compared to prior art hemoglobin.

To demonstrate the stability of the product from this invention, a heat stability test is performed at 80° C. The results are depicted in FIG. 15. The product made according to U.S. Pat. No. 7,494,974 and U.S. Pat. No. 7,504,377, shows a high met-hemoglobin content (22-28%). However, the product of the present invention shows a low level of met-hemoglobin (<5%).

Example 7

Packaging & Product Stability

Figure 16:
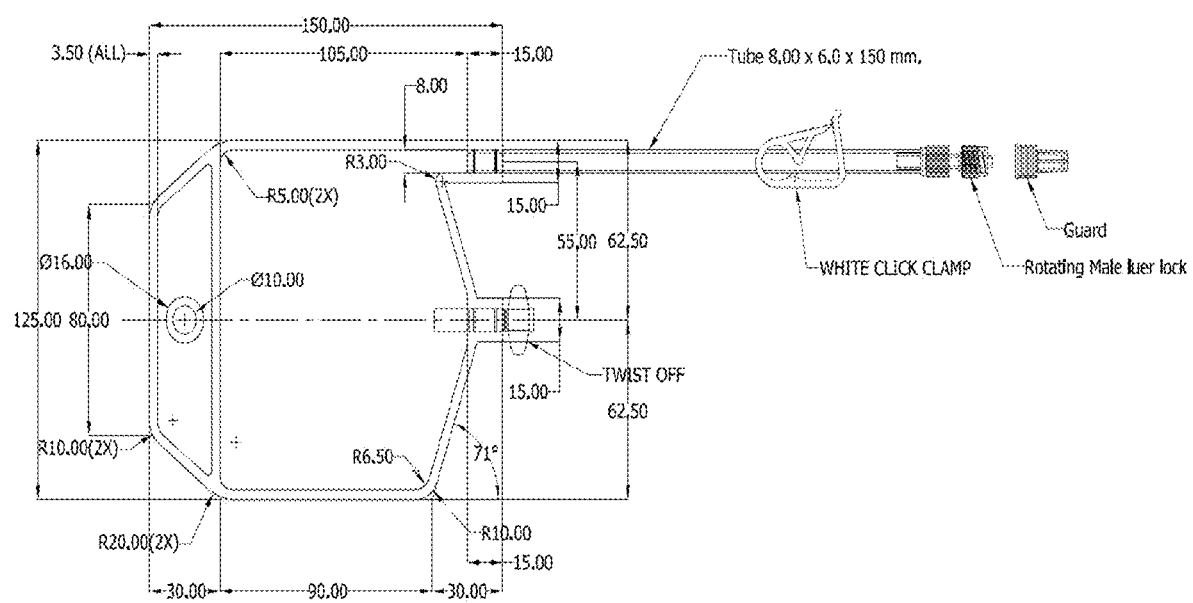
FIG. 16 is a schematic depiction of an infusion bag for the cross-linked tetrameric hemoglobin of the present invention.

Because the product of the present invention is stable under de-oxygenated conditions, the packaging for the product is important to minimize gas permeability. For intravenous application a custom designed, 100 mL infusion bag is made from a five layers EVA/EVOH laminated material with a thickness of 0.4 mm that has an oxygen permeability of 0.006 to 0.132 $cm^3$ per 100 square inches per 24 hours per atmosphere at room temperature. This specific material is a Class VI plastic (as defined in USP<88>), which meets the in-vivo biological reactivity tests and the physico-chemical test and are suitable for fabricating containers for intravenous injection purpose (note that other forms of packaging can be made from this material as well depending upon the desired application). A secondary packaging aluminum overwrap pouch is also applied to the primary packaging infusion bag that provides additional barrier in minimizing light exposure and oxygen diffusion. The composition of the pouch consists of: 0.012 mm of Polyethylene terephthalate (PET), 0.007 mm of Aluminum (AL), 0.015 mm of Nylon (NY) and 0.1 mm of Polyethylene (PE). The overwrap film has a thickness of 0.14 mm and oxygen transmission rate of 0.006 cm$^3$ per 100 square inches per 24 hours per atmosphere at room temperature. A schematic depiction of the infusion bag is depicted in FIG. 16. The overall oxygen permeability for each infusion bag from this present invention is 0.0025 cm$^3$ per 24 hours per atmosphere at room temperature.

A stability study is performed on the above packaging material at 40° C. and 75% relative humidity. The results are depicted in the following table 6. The results demonstrate that the packaging material maintains a low level of met-hemoglobin over an extended period.

TABLE 6

Stability Study
Conditions: Temperature 40 +/− 2° C., Relative humidity 75 +/− 5%

| Package Material | Time Points (month) | Total Hb (g/dL) | Met-Hb (%) | Oxy-Hb (%) | Endotoxin (EU/mL) |
|---|---|---|---|---|---|
| Infusion Bag & Aluminum Overwrap | 0 | 6.3 | 3.2 | 7.3 | <0.02 |
| | 1 | 6.3 | 1.0 | 6.8 | <0.02 |
| | 2 | 6.4 | 0.8 | 6.4 | <0.02 |
| | 3 | 6.3 | 0.8 | 6.6 | <0.02 |
| | 6 | 6.3 | 0.6 | 5.2 | <0.02 |

Example 8

Toxicity Study

Experiments are carried out to evaluate the potential toxicity of the purified cross-linked tetrameric hemoglobin of the present invention. 10 male Sprague-Dawley rats are assigned to 3 groups, 3 in control group, 3 in low dose group and 4 in high dose group. Normal saline (control), purified cross-linked tetrameric hemoglobin at a low dose (5.52 g/kg), purified cross-linked tetrameric hemoglobin at high dose (6.90 g/kg) are administered respectively to the rats via continuous intravenous infusion via the jugular vein at an infusion rate of 3 mL/kg/hr. The drug treatment schedule is shown in the following table 7. The cross-linked tetrameric hemoglobin is infused to the rats for up to 33.3 hours. The animals are closely observed for the duration of 9 days.

TABLE 7

| Study Groups | Control (n = 3) | Low Dose (n = 3) | High Dose (n = 4) |
|---|---|---|---|
| Day −7 to Day −6 | Surgery on animals and then NS infusion for 24 hours | | |
| Day −5 to Day −1 | Daily injection of heparin | | |
| Day 0 | Randomization and Acclimatization, NS infusion for 24 hours | | |
| Day 1 | Metabolic Analysis (Water and Urine) collection. NS Infusion | Metabolic Analysis (Water and Urine) collection. 26.7 hours Hb infusion and then 21.3 hours NS infusion | Metabolic Analysis (Water and Urine) collection. 33.3 hours Hb infusion and then 14.7 hours NS infusion |
| Day 2 | Metabolic Analysis (Water and Urine) collection | | |
| Day 3 | Metabolic Analysis (Water and Urine) collection | | |
| Day 4 | Stop NS infusion | | |
| Day 5 | Remove jacket and seal the tube, return animals to normal cages | | |
| Day 8 | Move Animal to metabolic cages for urine collection, and water consumed record | | |
| Day 9 | Metabolic Analysis (Water and Urine) collection Euthanasia of remaining animals Collection of blood (for both serum and plasma) Major organs preserved in formalin | | |

*NS: normal saline, Hb: cross-linked tetrameric hemoglobin

Blood samples are collected from all study animals for clinical pathology evaluations on Day 9. Urine is collected on Day 0 to Day 3 and Day 9 for urinalysis. Terminal necropsy is conducted on Day 9. Parameters evaluated include clinical observations, body weights, body weight changes, water consumption, clinical pathology (chematology, clinical chemistry and urinalysis), organ weights, organ-to-body weight ratio, organ-to-brain weight ratio, gross pathology and histopathology. Treatment with the cross-linked tetrameric hemoglobin of the present invention does not result in mortality or adverse clinical findings and no remarkable effects on body weight changes, and water consumption of rats.

There are no obvious changes observed on clinical chemistry and hematology parameters related to the treatment. Urine examination shows that the concentration of chloride and potassium is lower in treatment group than that of the control group on Day 2. Blood staining, higher protein concentration and more red blood cells in urine are found in treatment groups than control group on Day 2 to 3. Those observations all soon recover to normal. No significant difference is observed between lung-to-body weight ratio. During the study, no unexpected deaths and no obvious clinical signs of toxicity are observed. Additionally, gross pathological and histological analysis reveals no major abnormalities in all organs including lung, heart, liver, spleen and kidneys (such abnormalities are attributed to toxic side effects of infusion).

Example 9

Heart Preservation

Cross-linked tetrameric hemoglobin can be used as a cardioplegic solution in a model of heart preservation during cardiopulmonary bypass in Beagle dogs. 18 Beagle dogs are randomly divided into 3 groups: sham, St. Thomas' solution (STS), and 0.1% of cross-linked tetrameric hemoglobin groups. Cardiopulmonary bypass is established in a standard fashion with cannulation of the ascending aorta, superior and inferior vena cava, and left ventricle for venting. Except for the sham group, STS without (STS group) or with 0.1 g/dL cross-linked tetrameric hemoglobin (0.1% Hb group) are infused into the aortic root after aortic clamping to achieve cardiac arrest that is maintained for 120 minutes. The cardiac function, including cardiac output, pulmonary artery pressure, pulmonary artery wedge pressure, mean artery pressure, central venous pressure and heart rate, and the blood gas are measured during reperfusion and compared to baseline. The release of cardiac enzymes, including creatine kinase MB, lactate dehydrogenase and Troponin-1 are also measured as surrogate markers of cardiac injury. Hematoxylin and eosin staining and cardiac water content detection are performed to determine the morphological and pathological changes of myocardium 120 minutes after reperfusion.

Under the basal condition, the measures of the cardiac function, the oxygen consumption and the release of cardiac enzymes are similar among the 3 groups. During reperfusion, the heart rate, cardiac output and central venous pressure are greatly decreased in the STS group when compared to the sham group. However, the heart rate, cardiac output, central venous pressure and cardiac oxygen consumption are greatly preserved in 0.1% Hb group, which is similar to those of the sham group. The cross-linked tetrameric hemoglobin in STS also greatly reduces the appearance of lactate dehydrogenase, creatine kinase MB and troponin-I when compared to the STS group. Moreover, the cellular swelling, fatty changes and hyaline changes are significantly lessened in the 0.1% Hb group when compared to the STS group. The other measures, including pulmonary artery pressure, pulmonary artery wedge pressure, mean artery pressure and the cardiac water content, do not have significant differences among the 3 groups. All the measures in this study of the 0.1% Hb group have no significant difference as compared to the sham group. The 0.1 g/dL cross-linked tetrameric hemoglobin in STS during cardiopulmonary bypass exhibit a better cardiac protective effect than that of STS (a current standard cardioplegic solution) and the outcome is also comparable to the sham group.

Example 10

Figure 9:
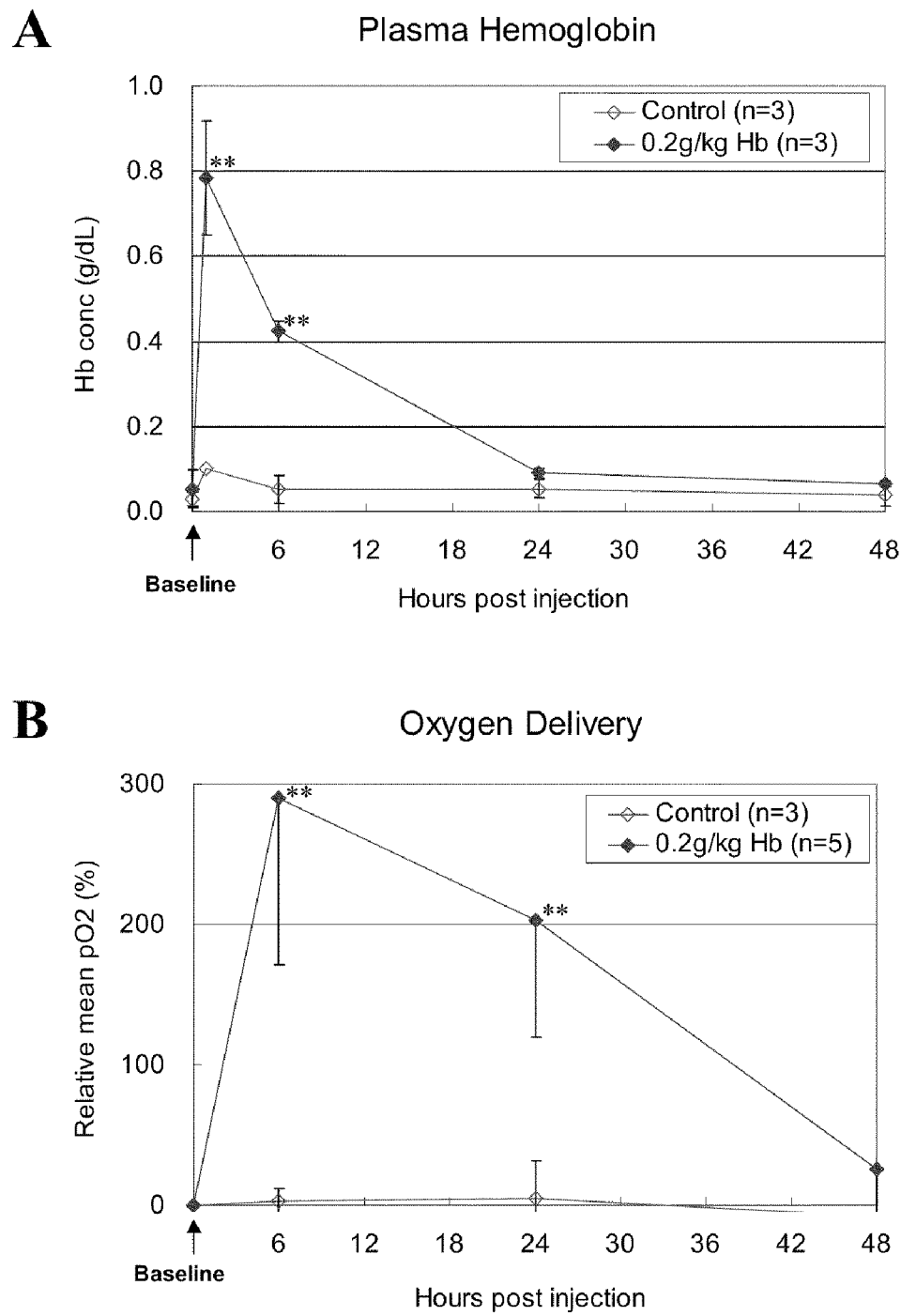
FIG. 9 depicts the improvement of oxygenation in normal tissue using the cross-linked tetrameric hemoglobin of the present invention.
Figure 10:
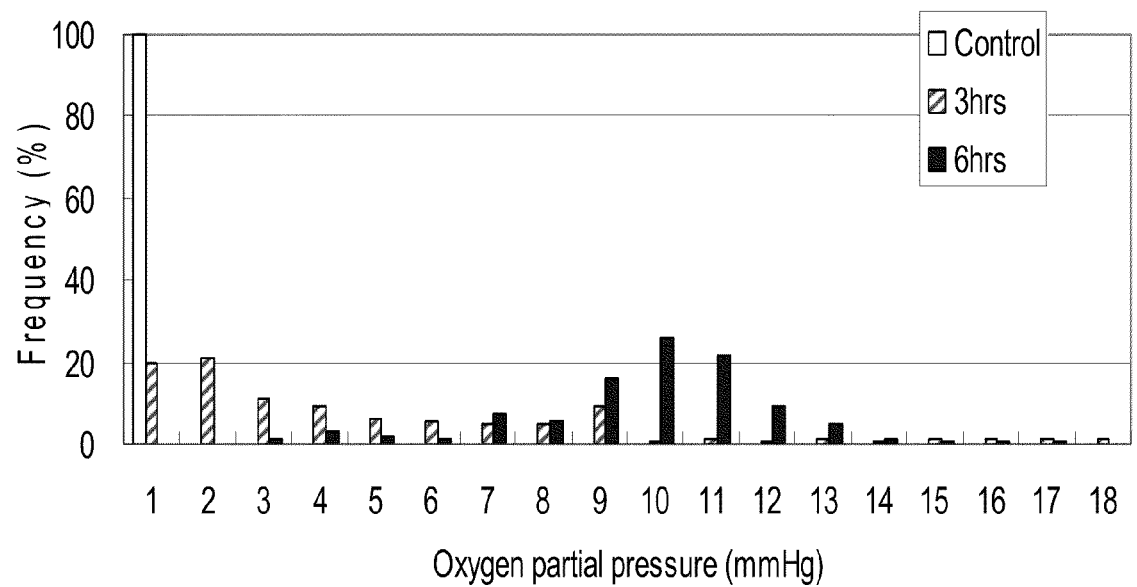
FIG. 10 shows the improvement of oxygenation in an extremely hypoxic tumor area using the cross-linked tetrameric hemoglobin of the present invention.

Studies on Tissue Oxygenation, Normal and Cancerous Tissues (10a) Improvement of Oxygenation in Normal Tissue Some studies for the normal tissue oxygenation by cross-linked tetrameric hemoglobin are carried out (as shown in FIG. 9). A comparative pharmacokinetic and pharmacodynamic study is conducted in buffalo rats. Male inbred buffalo rats are individually administered with 0.2 g/kg cross-linked tetrameric hemoglobin solution or ringer's acetate buffer (control group), through intravenous injection. The concentration-time profile of plasma hemoglobin is determined by Hemocue™ photometer at 1, 6, 24, 48 hours and compared with the baseline reading. The methods are based on photometric measurement of hemoglobin where the concentration of hemoglobin is directly read out as g/dL. Oxygen partial pressure (pO2) in the hind leg muscle of buffalo rats is directly measured by the Oxylab™ tissue oxygenation and temperature monitor (Oxford Optronix Limited). Rats are anesthetized by intra-peritoneal injection of 30-50 mg/kg pentobarbitone solution followed by insertion of the oxygen sensor into the muscle. All pO2 readings are recorded by Datatrax2 data acquisition system (World Precision Instrument) in a real-time manner.

As seen in FIG. 9, injection of 0.2 g/kg cross-linked tetrameric hemoglobin solution demonstrate a correlation between the pharmacokinetic (plasma hemoglobin concentration) and pharmacodynamic (delivery of oxygen to muscular tissue) properties of the inventive cross-linked tetrameric hemoglobin solution. Importantly, a significant increase in oxygenation is observed for a longer period of time compared with the plasma hemoglobin level. Plasma hemoglobin concentration is seen in graph (A) and oxygen delivery to muscle is seen in graph (B).

(10b) Improvement of Oxygenation in Extremely Hypoxic Tumor Area

Improvement of oxygenation in an extremely hypoxic tumor area is evaluated by a human nasopharyngeal carcinoma (CNE2) xenograft model. The CNE2 cell line is obtained from the Laboratory of Cancer Genetics, University of Hong Kong. Approximately $1 \times 10^6$ cancer cells are injected subcutaneously into 4- to 6-week-old inbred BALB/c AnN-nu (nude) mice. When the tumor xenograft reaches a diameter of 8-10 mm, oxygen partial pressure within the tumor mass is directly monitored by the Oxylab™ tissue oxygenation and temperature monitor (Oxford Optronix Limited). Oxygen partial pressure is measured along a tissue track with a fully computerized PTS30 Micro-positioning system (Discovery Technology International). All pO2 readings are recorded by the Datatrax2 data acquisition system (World Precision Instrument) in a real-time manner. When the pO2 reading is stabilized, 1.2 g/kg the inventive cross-linked tetrameric hemoglobin solution is injected intravenously through the tail vein of the mice and the tissue oxygenation is measured. Results demonstrate a significant increase of oxygenation in the most hypoxic tumor area. After intravenous injection of 1.2 g/kg of cross-linked tetrameric hemoglobin, the median pO2 value rise from 0.2 mmHg to 3.9 mmHg (in 3 hours) and 10.6 mmHg (in 6 hours), respectively (shown in FIG. 10).

Example 11

Cancer Treatment Study (Chemo-Sensitization Effects of Cross-Linked Tetrameric Hemoglobin)

The chemo-sensitization effects of the inventive cross-linked tetrameric hemoglobin are evaluated in different cancer cell lines. Leukemia cell line (Jurkat), colon cancer cell line (COL0205), cisplatin-resistant lung cancer cell line (A549/Cisp) and adriamycin-resistant breast cancer cell line (MCF-7/ADM) are obtained from Chinese Academy of Medical Sciences Cancer Institute. 8000 Jurkat cells, 4000 COL0205 cells, 3000 A549/Cisp cells and 3000 MCF-7/ADM cells are seeded individually in triplicate, onto a 96-well plate. After attachment, cells are incubated at 37° C. with various chemotherapeutic agents alone, or in conjunction with 0.5 mg/mL cross-linked tetrameric hemoglobin solution. Jurkat cells are treated with vincristine sulfate at 0.31, 0.63, 1.25, 2.5, 5 and 10 μg/mL; COL0205 cells are treated with 5-fluorouracil at 0.78, 1.56, 3.13, 6.25 and 12.5 μg/mL; A549/Cisp cells are treated with cisplatin at 0.39, 0.78, 1.56, 3.13, 6.25 and 12.5 μg/mL and MCF-7/ADM cells are treated with adriamycin at 0.39, 0.78, 1.56, 3.13, 6.25 and 12.5 μg/mL. After treatment, inhibition of cancer cell growth is determined by the ATP tumor chemo-sensitivity assay (ATP-TCA).

Esophageal cancer cell line HKESC-1 is obtained from Laboratory of Cancer Genetics, the University of Hong Kong.

2000 cancer cells are seeded onto a 96-well plate. After attachment, cells are incubated at 37° C. with cisplatin alone, at 0.08, 0.4, 2, 10 and 50 μg/mL, or in conjunction with 3 mg/mL cross-linked tetrameric hemoglobin solution. After incubation, cytotoxicity is evaluated by MTT cell proliferation assay. Results show that addition of the inventive cross-linked tetrameric hemoglobin significantly enhances chemosensitivity in various cancer cell lines including A549/Cisp and MCF-7/ADM cells that are highly resistant to chemotherapy (shown in FIG. 8).

Example 12

Treatment of Acute Severe Hemorrhagic Shock (12a) Treatment of Acute Severe Hemorrhagic Shock in Beagle Dogs The inventive cross-linked tetrameric hemoglobin is used as a resuscitation agent in a model of Acute Severe Hemorrhagic Shock in Beagle dogs. 60 Beagle dogs are randomly divided into 4 groups according to resuscitation agents, 15 dogs in each group.

Group 1: Dextran (Negative Control)

Group 2: Animal autologous blood (Positive Control)

Group 3: Low Dose Treatment (0.35 g cross-linked tetrameric hemoglobin/kg of body weight)

Group 4: Mid Dose Treatment (1.05 g cross-linked tetrameric hemoglobin/kg of body weight)

Acute severe hemorrhagic shock is established by withdrawing animal whole blood at a volume of 50 mL/kg body weight. Ten minutes after hemorrhagic shock established, Dextran (50 mL/kg), animal autologous blood (50 mL/kg), different doses of cross-linked tetrameric hemoglobin (5 mL/kg, 15 mL/kg) are infused into the animals. The infusion rate of cross-linked tetrameric hemoglobin is set at 10 mL/kg/h, hereafter, all experimental animals are observed for 7 days. A panel of parameters is observed and analyzed during the study period including survival, body weight, electro-cardiography (ECG), blood pressure, heart rate, respiration rate, body temperature, plasma hemoglobin concentration, hematology, arterial blood gas, urinalysis, clinical chemistry, coagulation, physical conditions and adverse events. Among all, survival is the primary end point. After seven days of treatment, the cross-linked tetrameric hemoglobin treatment group has a much higher survival rate compared with the normal group and the autologous blood group (as shown in the following table 8).

TABLE 8

Canine study in hemorrhagic shock model

| Group | Survival no. after 7 days (n = 15) | Survival rate after 7 days (%) |
|---|---|---|
| Dextran Negative Control | 7 | 46 |
| Dog's Autologous Blood | 12 | 80 |
| Low Dose Treatment | 14 | 97 |
| Mid Dose Treatment | 15 | 100 |

(12b) Treatment of Acute Severe Hemorrhagic Shock in Rats

The inventive cross-linked tetrameric hemoglobin is also used as a resuscitation agent in a model of Acute Severe Hemorrhagic Shock in rats. 80 Sprague-Dawley rats are randomly divided into 5 groups according to resuscitation agents, 16 rats in each group.

Group 1: Lactate Ringer's solution (Negative Control)

Group 2: Animal autologous blood (Positive Control)

Group 3: Low Dose Treatment (0.1 g cross-linked tetrameric hemoglobin/kg of body weight)

Group 4: Mid Dose Treatment (0.3 g cross-linked tetrameric hemoglobin/kg of body weight)

Group 5: High Dose Treatment (0.5 g cross-linked tetrameric hemoglobin/kg of body weight)

Acute severe hemorrhagic shock is established by withdrawing 50% of animal whole blood, which is estimated as 35 mL/kg of body weight. Ten minutes after hemorrhagic shock established, Lactate Ringer's solution, animal autologous blood, different doses of cross-linked tetrameric hemoglobin (0.1 g Hb/kg, 0.3 g Hb/kg, 0.5 g Hb/kg) are infused into the animals. The infusion rate of cross-linked tetrameric hemoglobin is set at 5 mL/h, hereafter, all experimental animals are observed for 24 hours. A panel of parameters is observed and analyzed during the study period including survival, hemodynamics, myocardial mechanics, cardiac output, cardiac function, blood gas, tissue oxygen delivery & consumption, tissue perfusion & oxygen tension (liver, kidney and brain), liver & renal function, hemorheology (blood viscosity), mitochondrial respiratory control rate (liver, kidney and brain). Among all, survival is the primary end point. After 24 hours of observation, the inventive cross-linked tetrameric hemoglobin treatment group has much higher survival rate compared with the normal group and the autologous blood group (shown in the following table 9).

TABLE 9

| Groups | Survival no. after 24-hour (n = 16) | 24-hour survival rate (%) |
|---|---|---|
| Negative control | 3 | 18.75 |
| Low Dose Treatment (0.1 g Hb/kg) | 6 | 37.5 |
| Mid Dose Treatment (0.3 g Hb/kg) | 8 | 50 |
| High Dose Treatment (0.5 g Hb/kg) | 12 | 75 |
| Rat's Autologous Blood | 10 | 62.5 |

*Hb: cross-linked tetrameric hemoglobin

Example 13

An In Vitro Met-Hemoglobin Formation Study

Figure 17:
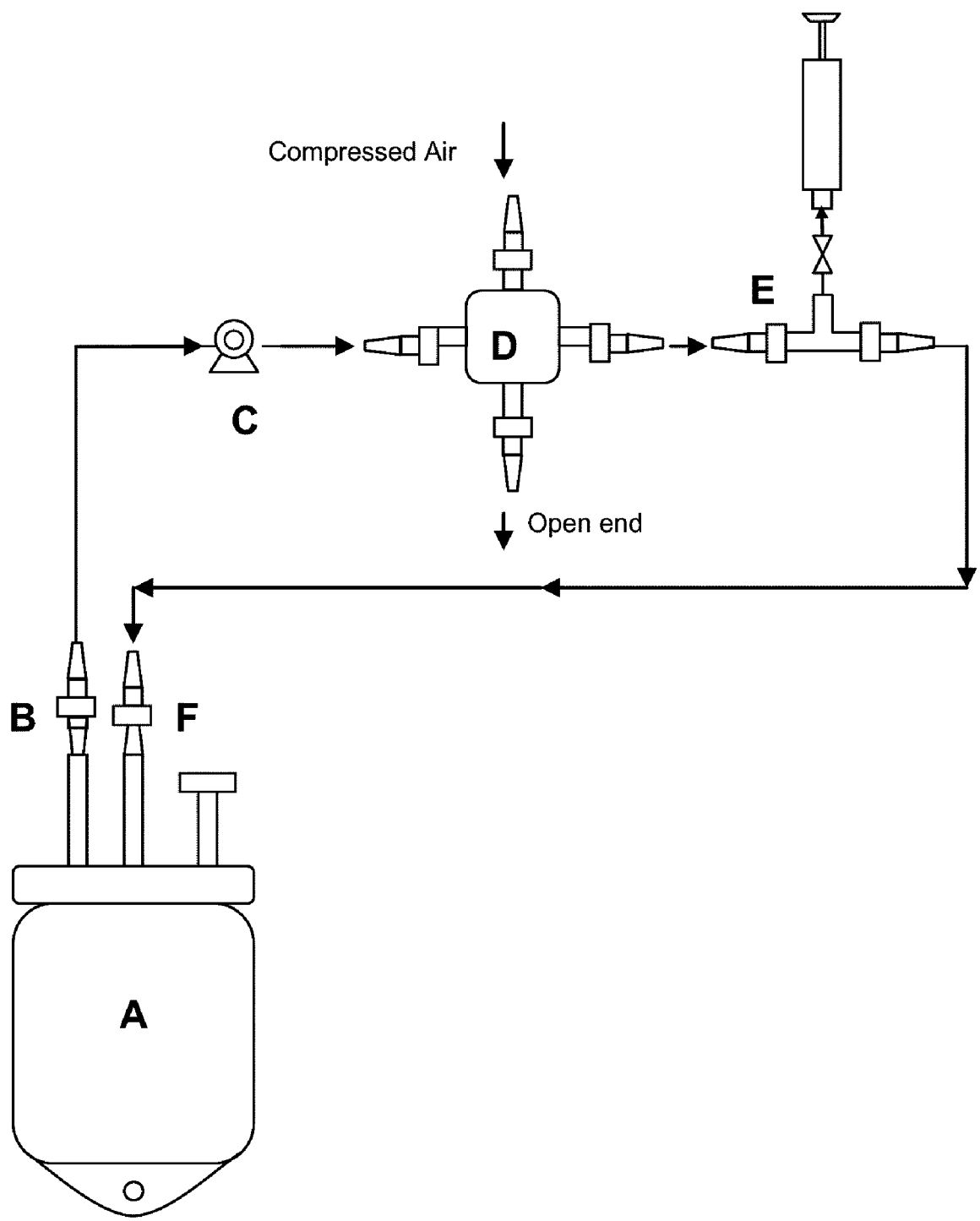
FIG. 17 is a schematic depiction of an apparatus used to test the formation of met-hemoglobin in vitro.

The prior art has stated that high molecular weight polymerized hemoglobin solution is preferable because it results in longer persistence in circulation. Therefore, the stabilized cross-linked tetrameric hemoglobin of the present invention is compared to high molecular weight polymerized hemoglobin in vitro to analyze stability in conditions that simulate circulation conditions. The test circuit is depicted in FIG. 17.

Figure 18:
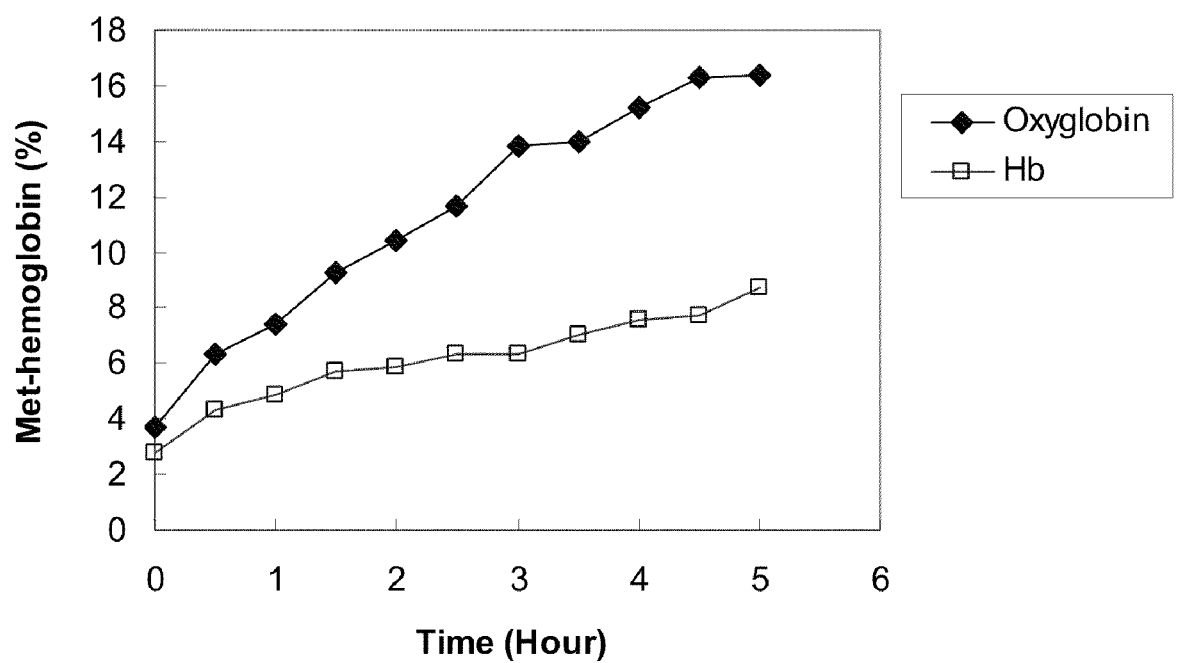
FIG. 18 depicts the rate of met-hemoglobin formation for polymeric hemoglobin and the inventive hemoglobin in the apparatus of FIG. 17.

In the met-hemoglobin formation by-pass circuit, A is the sample reservoir, B is the sample outlet port, C is the pump, D is Liqui-Cel contactor, E is a sample collection point and F is a sample inlet port. Time course met-hemoglobin formation of the cross-linked tetrameric hemoglobin solution of the present invention is compared with a commercially available product (Oxyglobin), which contains approximately 68% of polymeric fraction (≧128,000 MW). Before the experiment, all samples are diluted to 5 g/dL and 50 mL of diluted sample is introduced into the sample reservoir from the sample inlet port. The liquid pump rate is set at 30 mL/min, and the sample is allowed to fill the circuit. Throughout the experiment, the temperature of the sample reservoir is maintained at 37° C. To measure the met-hemoglobin level, 0.2 mL of test sample is collected from the sample collection point for co-oximetry (IL-682, Instrumentation Laboratory). Compressed air is then passed through the liqui-cel membrane contactor at flow rate 2.0 mL/min to start oxygenation of the samples. A 0.2 mL sample is collected at 30-minute intervals. After treatment for 5 hours, the met-hemoglobin fractions of the inventive cross-linked tetrameric hemoglobin solution and the commercial available product (Oxyglobin®) increase to 8.7% and 16.4%, respectively. This demonstrates that the inactive met-hemoglobin formation rate for polymeric hemoglobin is substantially greater than that for the inventive cross-linked tetrameric hemoglobin (FIG. 18).

While the foregoing invention has been described with respect to various embodiments, such embodiments are not limiting. Numerous variations and modifications would be understood by those of ordinary skill in the art. Such variations and modifications are considered to be included within the scope of the following claims.

What is claimed:

1. A method for the preparation of a highly purified and high-temperature stable oxygen-carrier-containing pharmaceutical composition, the oxygen-carrier-containing pharmaceutical composition including hemoglobin, the method comprising:
   a) providing mammalian whole blood including at least red blood cells and plasma;
   b) separating the red blood cells from the plasma in the mammalian whole blood;
   c) filtering the red blood cells that were separated from the plasma to obtain a filtered red blood cell fraction;
   d) washing the filtered red blood cell fraction to remove plasma protein impurities, resulting in washed red blood cells;
   e) disrupting the washed red blood cells by a controlled hypotonic lysis for a time sufficient to lyse red blood cells without lysing white blood cells in an instant cytolysis apparatus at a flow rate of at 50-1000 liter/hr to create a solution comprising a lysate of disrupted red blood cells;
   f) performing filtration to remove at least a portion of the waste retentate from the lysate;
   g) extracting a first hemoglobin solution from the lysate;
   h) performing a first ultrafiltration process using an ultrafiltration filter configured to remove impurities having a higher molecular weight than tetrameric hemoglobin to further remove any viruses and residual waste retentate from the first hemoglobin solution to obtain a second hemoglobin solution;
   i) performing flowthrough column chromatography on the second hemoglobin solution to remove phospholipids, protein impurities and dimeric hemoglobin and to form a phospholipid-free, low protein impurities and low dimer hemoglobin solution;
   j) performing a second ultrafiltration process on the phospholipid-free, low protein impurities and low dimer hemoglobin solution using a filter configured to remove impurities resulting in a concentrated purified phospholipid-free, low protein impurities and low dimer hemoglobin solution;
   k) blocking the sulfhydryl groups of hemoglobin molecules in the concentrated purified phospholipid-free, low protein impurities and low dimer hemoglobin solution by a sulfhydryl reagent in a fully oxygenated environment such that the hemoglobin molecules each have at least one cysteine moiety including a thiol-protecting group such that the hemoglobin molecules are incapable of binding endothelium-derived relaxing factor at the cysteine site;
   l) cross-linking the thiol-protected hemoglobin by bis-3,5-dibromosalicyl fumarate to form high-temperature stable cross-linked tetrameric hemoglobin without the formation of polymeric hemoglobin such that the molecular weight of the resultant cross-linked tetrameric hemoglobin is 60-70 kDa and consists essentially of nonpolymeric cross-linked tetrameric hemoglobin;
   m) exchanging a suitable physiological buffer for the cross-linked tetrameric hemoglobin;
   n) removing any residual non-cross-linked tetrameric hemoglobin and any residual chemicals by washing;
   o) adding N-acetyl cysteine at a concentration of 0.2-0.4% to the cross-linked tetrameric hemoglobin to maintain a level of met-hemoglobin below 5%; and
   p) adding the low dimer, phospholipid-free, thiol-protected high-temperature stable up to a temperature of 80° C.

cross-linked tetrameric hemoglobin free from polymeric hemoglobin to a pharmaceutically acceptable carrier.

2. The method for the preparation of the oxygen-carrier-containing pharmaceutical composition of claim 1 wherein the instant cytolysis apparatus includes a static mixer.

3. The method for the preparation of the oxygen-carrier-containing pharmaceutical composition of claim 1 wherein said cross-linked tetrameric hemoglobin is derived from bovine, porcine, canine or equine hemoglobin.

4. The method for the preparation of the oxygen-carrier-containing pharmaceutical composition of claim 1 wherein the column chromatography comprises one or more cation-exchange columns and anion-exchange columns.

5. The method for the preparation of the oxygen-carrier-containing pharmaceutical composition of claim 4 wherein the ion exchange columns are one or more DEAE column, CM column and/or hydroxyapatite column.

6. The method for the preparation of the oxygen-carrier-containing pharmaceutical composition of claim 1 wherein the hemoglobin cross-linking by bis-3,5-dibromosalicy fumarate includes at least $\alpha$-$\alpha$ and/or $\beta$-$\beta$ cross-linking.

7. The method for the preparation of an oxygen-carrier-containing pharmaceutical composition of claim 6 wherein the cross-linking conditions are selected such that $\beta$-$\beta$ cross-linking is greater than 50% of the total cross-linking.

8. The method for the preparation of an oxygen-carrier-containing pharmaceutical composition of claim 6 wherein the cross-linking conditions are selected such that $\beta$-$\beta$ cross-linking is greater than 60% of the total cross-linking.

9. The method for the preparation of an oxygen-carrier-containing pharmaceutical composition of claim 6 wherein the cross-linking conditions are selected such that $\beta$-$\beta$ cross-linking is greater than 70% of the total cross-linking.

10. The method for the preparation of an oxygen-carrier-containing pharmaceutical composition of claim 1 wherein the pharmaceutically acceptable carrier is a physiological buffer or water.

11. The method for the preparation of an oxygen-carrier-containing pharmaceutical composition of claim 1 further comprising packaging the prepared composition in a multi-layer, flexible infusion package having an oxygen permeability of less than 0.0025 $cm^3$ per 24 hours at ambient conditions.

12. A highly purified and high temperature stable oxygen carrier-containing pharmaceutical composition comprising hemoglobin, the hemoglobin consisting essentially of non-polymeric cross-linked tetrameric hemoglobin formed by the process of claim 1.

13. A method of oxygenating tissue comprising providing the composition of claim 12 to the tissue either in vivo or ex vivo.

* * * * *

SEQUENCE LISTING

```
<160> NUMBER OF SEQ ID NOS: 9

<210> SEQ ID NO 1
<211> LENGTH: 141
<212> TYPE: PRT
<213> ORGANISM: Bovine

<400> SEQUENCE: 1

Val Leu Ser Ala Ala Asp Lys Gly Asn Val Lys Ala Ala Trp Gly Lys
1               5                   10                  15

Val Gly Gly His Ala Ala Glu Tyr Gly Ala Glu Ala Leu Glu Arg Met
            20                  25                  30

Phe Leu Ser Phe Pro Thr Thr Lys Thr Tyr Phe Pro His Phe Asp Leu
        35                  40                  45

Ser His Gly Ser Ala Gln Val Lys Gly His Gly Ala Lys Val Ala Ala
    50                  55                  60

Ala Leu Thr Lys Ala Val Glu His Leu Asp Asp Leu Pro Gly Ala Leu
65                  70                  75                  80

Ser Glu Leu Ser Asp Leu His Ala His Lys Leu Arg Val Asp Pro Val
                85                  90                  95

Asn Phe Lys Leu Leu Ser His Ser Leu Leu Val Thr Leu Ala Ser His
            100                 105                 110

Leu Pro Ser Asp Phe Thr Pro Ala Val His Ala Ser Leu Asp Lys Phe
        115                 120                 125

Leu Ala Asn Val Ser Thr Val Leu Thr Ser Lys Tyr Arg
    130                 135                 140

<210> SEQ ID NO 2
<211> LENGTH: 142
<212> TYPE: PRT
<213> ORGANISM: Homo sapiens

<400> SEQUENCE: 2

Met Val Leu Ser Pro Ala Asp Lys Thr Asn Val Lys Ala Ala Trp Gly
1               5                   10                  15

Lys Val Gly Ala His Ala Gly Glu Tyr Gly Ala Glu Ala Leu Glu Arg
            20                  25                  30

Met Phe Leu Ser Phe Pro Thr Thr Lys Thr Tyr Phe Pro His Phe Asp
        35                  40                  45

Leu Ser His Gly Ser Ala Gln Val Lys Gly His Gly Lys Lys Val Ala
```

```
                    50                  55                  60
Asp Ala Leu Thr Asn Ala Val Ala His Val Asp Asp Met Pro Asn Ala
 65                  70                  75                  80

Leu Ser Ala Leu Ser Asp Leu His Ala His Lys Leu Arg Val Asp Pro
                     85                  90                  95

Val Asn Phe Lys Leu Leu Ser His Cys Leu Leu Val Thr Leu Ala Ala
                100                 105                 110

His Leu Pro Ala Glu Phe Thr Pro Ala Val His Ala Ser Leu Asp Lys
            115                 120                 125

Phe Leu Ala Ser Val Ser Thr Val Leu Thr Ser Lys Tyr Arg
        130                 135                 140
```

<210> SEQ ID NO 3
<211> LENGTH: 141
<212> TYPE: PRT
<213> ORGANISM: Canine

<400> SEQUENCE: 3

```
Val Leu Ser Pro Ala Asp Lys Thr Asn Ile Lys Ser Thr Trp Asp Lys
  1               5                  10                  15

Ile Gly Gly His Ala Gly Asp Tyr Gly Gly Glu Ala Leu Asp Arg Thr
                 20                  25                  30

Phe Gln Ser Phe Pro Thr Thr Lys Thr Tyr Phe Pro His Phe Asp Leu
             35                  40                  45

Ser Pro Gly Ser Ala Gln Val Lys Ala His Gly Lys Lys Val Ala Asp
         50                  55                  60

Ala Leu Thr Thr Ala Val Ala His Leu Asp Asp Leu Pro Gly Ala Leu
 65                  70                  75                  80

Ser Ala Leu Ser Asp Leu His Ala Tyr Lys Leu Arg Val Asp Pro Val
                 85                  90                  95

Asn Phe Lys Leu Leu Ser His Cys Leu Leu Val Thr Leu Ala Cys His
                100                 105                 110

His Pro Thr Glu Phe Thr Pro Ala Val His Ala Ser Leu Asp Lys Phe
            115                 120                 125

Phe Ala Ala Val Ser Thr Val Leu Thr Ser Lys Tyr Arg
        130                 135                 140
```

<210> SEQ ID NO 4
<211> LENGTH: 141
<212> TYPE: PRT
<213> ORGANISM: Porcine

<400> SEQUENCE: 4

```
Val Leu Ser Ala Ala Asp Lys Ala Asp Val Lys Ala Ala Tyr Gly Lys
  1               5                  10                  15

Val Gly Ala His Ala Gly Glu Ala Gly Ala Glu Ala Leu Glu Arg Met
                 20                  25                  30

Phe Leu Gly Phe Thr Thr Thr Lys Thr Tyr Phe Pro His Phe Asp Leu
             35                  40                  45

Ser His Gly Ser Asp Glu Val Lys Ala His Gly Glu Lys Val Ala Asp
         50                  55                  60

Ala Leu Thr Lys Ala Val Gly His Leu Asp Asp Met Pro Gly Ala Leu
 65                  70                  75                  80

Ser Ala Leu Ser Asp Leu His Ala His Lys Leu Arg Val Asp Pro Val
                 85                  90                  95

Asp Phe Lys Leu Leu Ser His Cys Leu Leu Ser Thr Leu Ala Val His
                100                 105                 110
```

Leu Pro Asp Asp Phe Thr Pro Ala Val His Ala Asp Leu Asp Lys Phe
        115                 120                 125

Leu Ala Asp Val Ser Thr Val Leu Asp Ser Lys Tyr Arg
        130                 135                 140

<210> SEQ ID NO 5
<211> LENGTH: 142
<212> TYPE: PRT
<213> ORGANISM: Equine

<400> SEQUENCE: 5

Met Val Leu Ser Ala Ala Asp Lys Thr Asn Val Lys Ala Ala Trp Ser
1               5                   10                  15

Lys Val Gly Gly His Ala Gly Glu Phe Gly Ala Glu Ala Leu Glu Arg
            20                  25                  30

Met Phe Leu Gly Phe Pro Thr Thr Lys Thr Tyr Phe Pro His Phe Asp
        35                  40                  45

Leu Ser His Gly Ser Ala Gln Val Lys Ala His Gly Lys Lys Val Gly
    50                  55                  60

Asp Ala Leu Thr Leu Ala Val Gly His Leu Asp Asp Leu Pro Gly Ala
65                  70                  75                  80

Leu Ser Asn Leu Ser Asp Leu His Ala His Lys Leu Arg Val Asp Pro
                85                  90                  95

Val Asn Phe Lys Leu Leu Ser His Cys Leu Leu Ser Thr Leu Ala Val
            100                 105                 110

His Leu Pro Asn Asp Phe Thr Pro Ala Val His Ala Ser Leu Asp Lys
        115                 120                 125

Phe Leu Ser Ser Val Ser Thr Val Leu Thr Ser Lys Tyr Arg
    130                 135                 140

<210> SEQ ID NO 6
<211> LENGTH: 145
<212> TYPE: PRT
<213> ORGANISM: Bovine

<400> SEQUENCE: 6

Met Leu Thr Ala Glu Glu Lys Ala Ala Val Thr Ala Phe Trp Gly Lys
1               5                   10                  15

Val Lys Val Asp Glu Val Gly Gly Glu Ala Leu Gly Arg Leu Leu Val
            20                  25                  30

Val Tyr Pro Trp Thr Gln Arg Phe Phe Glu Ser Phe Gly Asp Leu Ser
        35                  40                  45

Thr Ala Asp Ala Val Met Asn Asn Pro Lys Val Lys Ala His Gly Lys
    50                  55                  60

Lys Val Leu Asp Ser Phe Ser Asn Gly Met Lys His Leu Asp Asp Leu
65                  70                  75                  80

Lys Gly Thr Phe Ala Ala Leu Ser Glu Leu His Cys Asp Lys Leu His
                85                  90                  95

Val Asp Pro Glu Asn Phe Lys Leu Leu Gly Asn Val Leu Val Val Val
            100                 105                 110

Leu Ala Arg Asn Phe Gly Lys Glu Phe Thr Pro Val Leu Gln Ala Asp
        115                 120                 125

Phe Gln Lys Val Val Ala Gly Val Ala Asn Ala Leu Ala His Arg Tyr
    130                 135                 140

His
145

```
<210> SEQ ID NO 7
<211> LENGTH: 147
<212> TYPE: PRT
<213> ORGANISM: Homo sapiens

<400> SEQUENCE: 7

Met Val His Leu Thr Pro Glu Glu Lys Ser Ala Val Thr Ala Leu Trp
1               5                   10                  15

Gly Lys Val Asn Val Asp Glu Val Gly Gly Glu Ala Leu Gly Arg Leu
            20                  25                  30

Leu Val Val Tyr Pro Trp Thr Gln Arg Phe Phe Glu Ser Phe Gly Asp
        35                  40                  45

Leu Ser Thr Pro Asp Ala Val Met Gly Asn Pro Lys Val Lys Ala His
    50                  55                  60

Gly Lys Lys Val Leu Gly Ala Phe Ser Asp Gly Leu Ala His Leu Asp
65                  70                  75                  80

Asn Leu Lys Gly Thr Phe Ala Thr Leu Ser Glu Leu His Cys Asp Lys
                85                  90                  95

Leu His Val Asp Pro Glu Asn Phe Arg Leu Leu Gly Asn Val Leu Val
            100                 105                 110

Cys Val Leu Ala His His Phe Gly Lys Glu Phe Thr Pro Pro Val Gln
        115                 120                 125

Ala Ala Tyr Gln Lys Val Val Ala Gly Val Ala Asn Ala Leu Ala His
    130                 135                 140

Lys Tyr His
145

<210> SEQ ID NO 8
<211> LENGTH: 147
<212> TYPE: PRT
<213> ORGANISM: Porcine

<400> SEQUENCE: 8

Met Val His Leu Ser Ala Glu Glu Lys Glu Ala Val Leu Gly Leu Trp
1               5                   10                  15

Gly Lys Val Asn Val Asp Glu Val Gly Gly Glu Ala Leu Gly Arg Leu
            20                  25                  30

Leu Val Val Tyr Pro Trp Thr Gln Arg Phe Phe Glu Ser Phe Gly Asp
        35                  40                  45

Leu Ser Asn Ala Asp Ala Val Met Gly Asn Pro Lys Val Lys Ala His
    50                  55                  60

Gly Lys Lys Val Leu Gln Ser Phe Ser Asp Gly Leu Lys His Leu Asp
65                  70                  75                  80

Asn Leu Lys Gly Thr Phe Ala Lys Leu Ser Glu Leu His Cys Asp Gln
                85                  90                  95

Leu His Val Asp Pro Glu Asn Phe Arg Leu Leu Gly Asn Val Ile Val
            100                 105                 110

Val Val Leu Ala Arg Arg Leu Gly His Asp Phe Asn Pro Asn Val Gln
        115                 120                 125

Ala Ala Phe Gln Lys Val Val Ala Gly Val Ala Asn Ala Leu Ala His
    130                 135                 140

Lys Tyr His
145

<210> SEQ ID NO 9
<211> LENGTH: 147
<212> TYPE: PRT
```

-continued

```
<213> ORGANISM: Equine

<400> SEQUENCE: 9

Met Val Gln Leu Ser Gly Glu Glu Lys Ala Ala Val Leu Ala Leu Trp
1               5                   10                  15

Asp Lys Val Asn Glu Glu Val Gly Gly Glu Ala Leu Gly Arg Leu
                20                  25                  30

Leu Val Val Tyr Pro Trp Thr Gln Arg Phe Phe Asp Ser Phe Gly Asp
            35                  40                  45

Leu Ser Asn Pro Gly Ala Val Met Gly Asn Pro Lys Val Lys Ala His
        50                  55                  60

Gly Lys Lys Val Leu His Ser Phe Gly Glu Gly Val His His Leu Asp
65                  70                  75                  80

Asn Leu Lys Gly Thr Phe Ala Ala Leu Ser Glu Leu His Cys Asp Lys
                85                  90                  95

Leu His Val Asp Pro Glu Asn Phe Arg Leu Leu Gly Asn Val Leu Val
                100                 105                 110

Val Val Leu Ala Arg His Phe Gly Lys Asp Phe Thr Pro Glu Leu Gln
            115                 120                 125

Ala Ser Tyr Gln Lys Val Val Ala Gly Val Ala Asn Ala Leu Ala His
        130                 135                 140

Lys Tyr His
145
```